United States Patent [19]

Ciccarone et al.

[11] Patent Number: 5,578,629
[45] Date of Patent: Nov. 26, 1996

[54] BENZAMIDE-CONTAINING INHIBITORS OF FARNESYL-PROTEIN TRANSFERASE

[75] Inventors: Terrence M. Ciccarone, Telford; Theresa M. Williams, Harleysville; Suzanne C. MacTough, Chalfont, all of Pa.

[73] Assignee: Merck & Co., Inc., Rahway, N.J.

[21] Appl. No.: 413,137

[22] Filed: Mar. 29, 1995

[51] Int. Cl.$^6$ .................. C07D 277/04; C07D 277/12; C07C 237/20; C07C 323/29; C07C 321/10
[52] U.S. Cl. .................. 514/397; 514/399; 514/562; 548/312.7; 548/338.1; 562/428
[58] Field of Search .................. 548/338.1, 312.7; 562/428; 514/397, 399, 562

[56] References Cited

U.S. PATENT DOCUMENTS

| | | | |
|---|---|---|---|
| 5,043,268 | 8/1991 | Stock | 435/15 |
| 5,141,851 | 8/1992 | Brown et al. | 435/15 |
| 5,179,117 | 1/1993 | Maduskuie | 514/398 |
| 5,238,922 | 8/1993 | Graham et al. | 514/18 |
| 5,256,645 | 10/1993 | Branca et al. | 514/18 |
| 5,326,773 | 7/1994 | De Solms et al. | 514/336 |
| 5,340,828 | 8/1994 | Graham et al. | 514/367 |
| 5,352,705 | 10/1994 | Deana et al. | 514/630 |

FOREIGN PATENT DOCUMENTS

| | | | |
|---|---|---|---|
| 0456180A1 | 11/1991 | European Pat. Off. | 514/357 |
| 5-17419 | 1/1993 | Japan | 548/338.1 |
| WO91/16340 | 10/1991 | WIPO | 514/18 |
| 94-19326 | 9/1994 | WIPO | 548/338.1 |
| WO95/11917 | 5/1995 | WIPO | 514/357 |
| WO95/25086 | 9/1995 | WIPO | 560/17 |

OTHER PUBLICATIONS

Gibbs, J. B. et al., "Selective Inhibition of Farnesyl–Protein Transferase Blocks Ras Processing in Vivo", The Journal of Biological Chemistry, vol. 268, No. 11, pp. 7617–7620 (1993).
Goldstein, J. L. et al., "Nonfarnesylated Tetrapeptide Inhibitors of Protein Farnesyltransferase", The Journal of Biological Chemistry, vol. 266, No. 24 pp. 15575–15578 (1991).
James, G. L. et al., "Benzodiazepine Peptidomimetic SZA-S8 Interrupts the MAP Kinase Activation Pathway in H–Res-transformed Rat-1 Cells, but Not in Untransformed Cells", The Journal of Biological Chemistry, vol. 369, No. 44, pp. 27705–27714 (1994).
James, G. L. et al., "Benzodiazepine Peptidomimetics: Potent Inhibitors of Ras Farnesylation in Animal Cells", Science, vol. 260, pp. 1937–1942 (1993).
James, G., et al., "Polylysine and CVIM Sequences of K–RasB Dictate Specificity of Prenylation and Confer Resistance to Benzodiazepine Peptidomimetic in Vitro", The Journal of Biological Chemistry, vol. 270, No. 11, pp. 6221–6226 (1995).
Kohl, N. E. et al., "Selective Inhibition of ras–Dependent Transformation by a Farnesyltransferase Inhibitor", Science, vol. 260, pp. 1934–1937 (1993).
Kohl, N. E. et al., "Protein farnesyltransferase inhibitors block the growth of ras–dependent tumors in nude mice", Proc. Natl. Acad. Sci. USA, Med. Sciences, vol. 91, pp. 9141–9145 (1994).
Nlgam, M., et al., "Potent Inhibition of Human Tumor p21 ras Farnesyltransferase by A1A2-lacking p21 ras CA1A2X Peptidomimetics", The Journal of Biol. Chem., vol. 268, Issue of Oct. 5, pp. 20695–20698 (1993).
Pompliano, D. L., "Steady–State Kinetic Mechanism of Ras Farnesyl:Protein Transferase", Biochemistry, vol. 31, pp. 3800–3807 (1992).
Qian, T., et al., "Design and Structural Requirements of Potent Peptidomimetic Inhibitors of p21 ras Farnesyltransferase", The Journal of Biol. Chem., vol. 269, No. 17, Issue of Apr. 29, pp. 12410–12413 (1994).
Vogt, A., et al., "A Non–peptide Mimetic of Ras–CAAX: Selective Inhibition of Farnesyltransferase and Ras Processing", The Journal of Biol. Chem., vol. 270, No. 2, Issue of Jan. 13, pp. 660–664 (1995).

*Primary Examiner*—Floyd D. Higel
*Attorney, Agent, or Firm*—David A. Muthard; Mark R. Daniel

[57] ABSTRACT

The present invention comprises peptidomimetic compounds which comprise a suitably substituted aminoalkylbenzamide moiety. The instant compounds inhibit the farnesyl protein transferase enzyme and the farnesylation of certain proteins. Furthermore, the instant farnesyl protein transferase inhibitors differ from those previously described as inhibitors of farnesyl-protein transferase in that they do not have a thiol moiety. The lack of the thiol offers unique advantages in terms of improved pharmacokinetic behavior in animals, prevention of thiol-dependent chemical reactions, such as rapid autoxidation and disulfide formation with endogenous thiols, and reduced systemic toxicity. Further contained in this invention are chemotherapeutic compositions containing these farnesyl transferase inhibitors and methods for their production.

17 Claims, No Drawings

BENZAMIDE-CONTAINING INHIBITORS OF FARNESYL-PROTEIN TRANSFERASE

BACKGROUND OF THE INVENTION

The Ras protein is part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, *Ann. Rev. Biochem.* 62:851–891 (1993)). Mutated ras genes are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., *Nature* 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., *Ann. Rev. Biochem.* 61:355–386 (1992); W. R. Schafer and J. Rine, *Ann. Rev. Genetics* 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., *J. Biol. Chem.* 269, 14182 (1994) have identified a peroxisome associated protein Pxf which is also farnesylated. James, et al., have also suggested that there are farnesylated proteins of unknown structure and function in addition to those listed above Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., *Science*, 260:1934–1937 (1993) and G. L. James et al., *Science*, 260:1937–1942 (1993). Recently, it has been shown that an inhibitor of farnesyl-protein transferase blocks the growth of ras-dependent tumors in nude mice (N. E. Kohl et al., *Proc. Natl. Acad. Sci U.S.A.*, 91:9141–9145 (1994).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., *Cell* 62:81–88 (1990); Schaber et al., *J. Biol. Chem.*, 265:14701–14704 ( 1990); Schafer et al., *Science*, 249:1133–1139 (1990); Manne et al., *Proc. Natl. Acad. Sci USA*, 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase (FPTase) have been described in two general classes. The first are analogs of farnesyl diphosphate (FPP), while the second class of inhibitors is related to the protein substrates (e.g., Ras) for the enzyme. In the peptide derived class of inhibitors, a subclass of inhibitors has been described which generally comprises cysteine containing molecules that are related to the CAAX motif that is the signal for protein prenylation. (Schaber et al., ibid; Reiss et. al., ibid; Reiss et al., *PNAS*, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., *Science*, 260:1934–1937 (1993); Graham, et al., *J. Med. Chem.*, 37, 725 (1994)). In general, deletion of the thiol from a peptidyl CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity. Therefore, a functional replacement for the thiol is desirable. With the exception of a group of antibiotics known as the pepticinnamins (Omura, et al., *J. Antibiotics* 46:222 (1993)), non-thiol FPTase inhibitors that are competitive with the Ras substrate have not been described.

Another subclass of the peptide derived inhibitors which comprises peptidomimetic compounds wherein the central AA portion of the CAAX motif has been replaced by 3-aminobenzoic acid and 3-aminomethylbenzoic acid spacers has recently been described (M. Nigam et al. *J. Biol. Chem.*, 268:20695–20698 (1993), Y. Qian et al. *J. Biol. Chem.*, 269:12410–12413 (1994)). FPTase peptidomimetic inhibitors further lacking a C-terminus peptidyl moiety (wherein the X peptide has been replaced by a non-peptide moiety) have also been recently described (A. Vogt et al. *J. Biol. Chem.*, 270:660–664 (1995)). All of the compounds in this second subclass of peptide derived inhibitors retain the thiol moiety.

It is, therefore, an object of this invention to develop non-peptide compounds that do not have a thiol moiety, and that will inhibit farnesyl-protein transferase and thus, the post-translational farnesylation of proteins. It is a further object of this invention to develop chemotherapeutic compositions containing the compounds of this invention and methods for producing the compounds of this invention.

SUMMARY OF THE INVENTION

The present invention includes substituted aminoalkylbenzamide and aminobenzamide analogs which inhibit the farnesyl-protein transferase, chemotherapeutic compositions containing the compounds of this invention, and methods for producing the compounds of this invention. Furthermore these analogs differ from those previously described as inhibitors of farnesyl-protein transferase in that they do not have a thiol moiety. The lack of the thiol offers unique advantages in terms of improved pharmacokinetic behavior in animals, prevention of thiol-dependent chemical reactions, such as rapid autoxidation and disulfide formation with endogenous thiols, and reduced systemic toxicity.

The compounds of this invention are illustrated by the formulae:

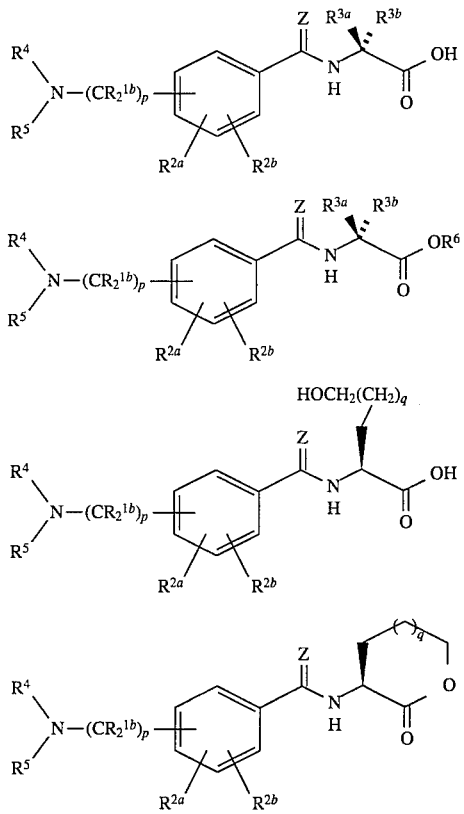

DETAILED DESCRIPTION OF THE INVENTION

The compounds of this invention are useful in the inhibition of farnesyl-protein transferase and the farnesylation of certain proteins.

In a first embodiment of this invention, the farnesyl-protein transferase inhibitors are illustrated by the formula I:

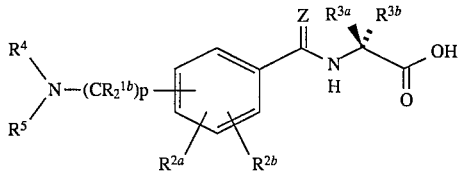

wherein:

$R^{1a}$ and $R^{1b}$ are independently selected from:

a) hydrogen, b) aryl, heterocycle, cycloalkyl, alkenyl, alkynyl, $R^{10}O—$, $R^{11}S(O)_m—$, $R^{10}C(O)NR^{10}—$, CN, $NO_2$, $(R^{10})_2N—C(NR^{10})—$, $R^{10}C(O)—$, $R^{10}OC(O)—$, $N_3$, $—N(R^{10})_2$, or $R^{11}OC(O)NR^{10}—$, c) $C_1$–$C_6$ alkyl unsubstituted or substituted by aryl, heterocycle, cycloalkyl, alkenyl, alkynyl, $R^{10}O—$, $R^{11}S(O)_m—$, $R^{10}C(O)NR^{10}—$, CN, $(R^{10})_2N—C(NR^{10})—$, $R^{10}C(O)—$, $R^{10}OC(O)—$, $N_3$, $—N(R^{10})_2$, or $R^{11}OC(O)—NR^{10}—$;

$R^{2a}$ and $R^{2b}$ are independently selected from:

a) hydrogen, b) $C_1$–$C_6$ alkyl unsubstituted or substituted by alkenyl, $R^{10}O—$, $R^{11}S(O)_m—$, $R^{10}C(O)NR^{10}—$, CN, $N_3$, $(R^{10})_2N—C(NR^{10})—$, $R^{10}C(O)—$, $R^{10}OC(O)—$, $—N(R^{10})_2$, or $R^{11}OC(O)NR^{10}—$, c) aryl, heterocycle, cycloalkyl, alkenyl, $R^{10}O—$, $R^{11}S(O)_m—$, $R^{10}C(O)NR^{10}—$, CN, $NO_2$, $(R^{10})_2N—C(NR^{10})—$, $R^{10}C(O)—$, $R^{10}OC(O)—$, $N_3$, $—N(R^{10})_2$, or $R^{11}OC(O)NR^{10}—$, and d) $C_1$–$C_6$ alkyl substituted with an unsubstituted or substituted group selected from aryl, heterocyclic and $C_3$–$C_{10}$ cycloalkyl;

$R^{3a}$ and $R^{3b}$ are independently selected from:

a) a side chain of a naturally occurring amino acid, b) an oxidized form of a side chain of a naturally occurring amino acid which is:
i) methionine sulfoxide, or
ii) methionine sulfone, and c) substituted or unsubstituted $C_1$–$C_{20}$ alkyl, $C_2$–$C_{20}$ alkenyl, $C_3$–$C_{10}$ cycloalkyl, aryl or heterocyclic group, wherein the substituent is selected from F, Cl, Br, $N(R^{10})_2$, $NO_2$, $R^{10}O—$, $R^{11}S(O)_m—$, $R^{10}C(O)NR^{10}—$, CN, $(R^{10})_2N—C(NR^{10})—$, $R^{10}C(O)—$, $R^{10}OC(O)—$, $N_3$, $—N(R^{10})_2$, $R^{11}OC(O)NR^{10}—$ and $C_1$–$C_{20}$ alkyl, and d) $C_1$–$C_6$ alkyl substituted with an unsubstituted or substituted group selected from aryl, heterocycle and $C_3$–$C_{10}$ cycloalkyl; or $R^{3a}$ and $R^{3b}$ are combined to form $—(CH_2)_s—$ wherein one of the carbon atoms is optionally replaced by a moiety selected from: O, $S(O)_m$, $—NC(O)—$, and $—N(COR^{10})—$;

$R^4$ and $R^5$ are independently selected from:

a) hydrogen, and b)

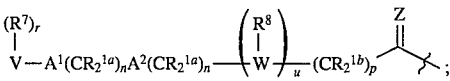

$R^7$ is independently selected from:

a) hydrogen, b) aryl, heterocycle, cycloalkyl, alkenyl, alkynyl, perfluoroalkyl, F, Cl, Br, $R^{10}O—$, $R^{11}S(O)_m—$, $R^{10}C(O)NR^{10}—$, CN, $NO_2$, $R^{10}_2N—C(NR^{10})—$, $R^{10}C(O)—$, $R^{10}OC(O)—$, $N_3$, $—N(R^{10})_2$, or $R^{11}OC(O)NR^{10}—$, and c) $C_1$–$C_6$ alkyl unsubstituted or substituted by aryl, heterocycle, cycloalkyl, alkenyl, alkynyl, perfluoroalkyl, F, Cl, Br, $R^{10}O—$, $R^{11}S(O)_m—$, $R^{10}C(O)NH—$, CN, $H_2N—C(NH)—$, $R^{10}C(O)—$, $R^{10}OC(O)—$, $N_3$, $—N(R^{10})_2$, or $R^{10}OC(O)NH—$;

$R^8$ is selected from:

a) hydrogen, b) alkenyl, alkynyl, perfluoroalkyl, F, Cl, Br, $R^{10}O—$, $R^{11}S(O)_m—$, $R^{10}C(O)NR^{10}—$, CN, $NO_2$, $(R^{10})_2N—C—(N^{R10})—$, $R^{10}C(O)—$, $R^{10}OC(O)—$, $N_3$, $—N(R^{10})_2$, or $R^{11}OC(O)NR^{10}—$, and c) $C_1$–$C_6$ alkyl unsubstituted or substituted by perfluoroalkyl, F, Cl, Br, $R^{10}O—$, $R^{11}S(O)_m—$, $R^{10}C(O)NR^{10}—$, CN, $(R^{10})_2N—C(NR^{10})—$, $R^{10}C(O)—$, $R^{10}OC(O)—$, $N_3$, $—N(R^{10})_2$, or $R^{11}OC(O)NR^{10}—$;

$R^{10}$ is independently selected from hydrogen, $C_1$–$C_6$ alkyl, benzyl and aryl;

$R^{11}$ is independently selected from $C_1$–$C_6$ alkyl and aryl;
$A^1$ and $A^2$ are independently selected from: a bond, —CH=CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, or S(O)$_m$;

V is selected from:
a) hydrogen,
b) heterocycle,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl,
provided that V is not hydrogen if $A^1$ is S(O)$_m$ and V is not hydrogen if $A^1$ is a bond, n is 0 and $A^2$ is S(O)$_m$;

W is a heterocycle;
Z is independently $H_2$ or O;
m is 0, 1 or 2;
n is 0, 1, 2, 3 or 4;
p is 0, 1, 2, 3 or 4;
r is 0 to 5, provided that r is 0 when V is hydrogen;
s is 4 or 5; and
u is 0 or 1;
or the pharmaceutically acceptable salts thereof.

In a second embodiment of this invention the prodrugs of compounds of formula I are illustrated by the formula II:

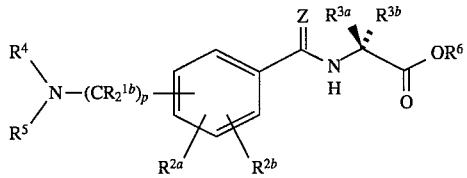

wherein:
$R^{1a}$ and $R^{1b}$ are independently selected from:
a) hydrogen,
b) aryl, heterocycle, cycloalkyl, alkenyl, alkynyl, $R^{10}$O—, $R^{11}$S(O)$_m$—, $R^{10}$C(O)NR$^{10}$—, CN, NO$_2$, (R$^{10}$)$_2$N—C(NR$^{10}$)—, $R^{10}$C(O)—, $R^{10}$OC(O)—, N$_3$, —N(R$^{10}$)$_2$, or $R^{11}$OC(O)NR$^{10}$—,
c) $C_1$–$C_6$ alkyl unsubstituted or substituted by aryl, heterocyclic, cycloalkyl, alkenyl, alkynyl, $R^{10}$O—, $R^{11}$S(O)$_m$—, $R^{10}$C(O)NR$^{10}$—, CN, (R$^{10}$)$_2$N—C(NR$^{10}$)—, $R^{10}$C(O)—, $R^{10}$OC(O)—, N$_3$, —N(R$^{10}$)$_2$, or $R^{11}$OC(O)—NR$^{10}$—;

$R^{2a}$ and $R^{2b}$ are independently selected from:
a) hydrogen,
b) $C_1$–$C_6$ alkyl unsubstituted or substituted by alkenyl, $R^{10}$O—, $R^{11}$S(O)$_m$—, $R^{10}$C(O)NR$^{10}$—, CN, N$_3$, (R$^{10}$)$_2$N—C(NR$^{10}$)—, $R^{10}$C(O)—, $R^{10}$OC(O)—, —N(R$^{10}$)$_2$, or $R^{11}$OC(O)NR$^{10}$—,
c) aryl, heterocycle, cycloalkyl, alkenyl, $R^{10}$O—, $R^{11}$S(O)$_m$—, $R^{10}$C(O)NR$^{10}$—, CN, NO$_2$, (R$^{10}$)$_2$N—C(NR$^{10}$)—, $R^{10}$C(O)—, $R^{10}$OC(O)—, N$_3$, —N(R$^{10}$)$_2$, or $R^{11}$OC(O)NR$^{10}$—, and
d) $C_1$–$C_6$ alkyl substituted with an unsubstituted or substituted group selected from aryl, heterocyclic and $C_3$–$C_{10}$ cycloalkyl;

$R^{3a}$ and $R^{3b}$ are independently selected from:
a) a side chain of a naturally occurring amino acid,
b) an oxidized form of a side chain of a naturally occurring amino acid which is:
  i) methionine sulfoxide, or
  ii) methionine sulfone, and c) substituted or unsubstituted $C_1$–$C_{20}$ alkyl, $C_2$–$C_{20}$ alkenyl, $C_3$–$C_{10}$ cycloalkyl, aryl or heterocyclic group, wherein the substituent is selected from F, Cl, Br, N(R$^{10}$)$_2$, NO$_2$, $R^{10}$O—, $R^{11}$S(O)$_m$—, $R^{10}$C(O)NR$^{10}$—, CN, (R$^{10}$)$_2$N—C(NR$^{10}$)—, $R^{10}$C(O)—, $R^{10}$OC(O)—, N$_3$, —N(R$^{10}$)$_2$, $R^{11}$OC(O)NR$^{10}$— and $C_1$–$C_{20}$ alkyl, and
d) $C_1$–$C_6$ alkyl substituted with an unsubstituted or substituted group selected from aryl, heterocycle and $C_3$–$C_{10}$ cycloalkyl; or $R^{3a}$ and $R^{3b}$ are combined to form —(CH$_2$)$_s$— wherein one of the carbon atoms is optionally replaced by a moiety selected from: O, S(O)$_m$, —NC(O)—, and —N(COR$^{10}$)—;

$R^4$ and $R^5$ are independently selected from:
a) hydrogen, and
b)

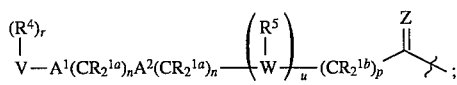

$R^6$ is
a) substituted or unsubstituted $C_1$–$C_8$ alkyl or substituted or unsubstituted $C_5$–$C_8$ cycloalkyl, wherein the substituent on the alkyl is selected from:
1) aryl,
2) heterocycle,
3) —N(R$^{11}$)$_2$,
4) —OR$^{10}$, or
b)

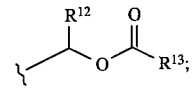

$R^7$ is independently selected from:
a) hydrogen,
b) aryl, heterocycle, cycloalkyl, alkenyl, alkynyl, perfluoroalkyl, F, Cl, Br, $R^{10}$O—, $R^{11}$S(O)$_m$—, $R^{10}$C(O)NR$^{10}$—, CN, NO$_2$, $R^{10}$$_2$N—C(NR$^{10}$)—, $R^{10}$C(O)—, $R^{10}$OC(O)—, N$_3$, —N(R$^{10}$)$_2$, or $R^{11}$OC(O)NR$^{10}$—, and
c) $C_1$–$C_6$ alkyl unsubstituted or substituted by aryl, heterocycle, cycloalkyl, alkenyl, alkynyl, perfluoroalkyl, F, Cl, Br, $R^{10}$O—, $R^{11}$S(O)$_m$—, $R^{10}$C(O)NH—, CN, H$_2$N—C(NH)—, $R^{10}$C(O)—, $R^{10}$OC(O)—, N$_3$, —N(R$^{10}$)$_2$, or $R^{10}$OC(O)NH—;

R8 is selected from:
a) hydrogen,
b) alkenyl, alkynyl, perfluoroalkyl, F, Cl, Br, $R^{10}$O—, $R^{11}$S(O)$_m$—, $R^{10}$C(O)NR$^{10}$—, CN, NO$_2$, (R$^{10}$)$_2$N—C—(NR$^{10}$)—, $R^{10}$C(O)—, $R^{10}$OC(O)—, N$_3$, —N(R$^{10}$)$_2$, or $R^{11}$OC(O)NR$^{10}$—, and
c) $C_1$–$C_6$ alkyl unsubstituted or substituted by perfluoroalkyl, F, Cl, Br, $R^{10}$O—, $R^{11}$S(O)$_m$—, $R^{10}$C(O)NR$^{10}$—, CN, (R$^{10}$)$_2$N—C(NR$^{10}$)—, $R^{10}$C(O)—, $R^{10}$OC(O)—, N$_3$, —N(R$^{10}$)$_2$, or $R^{11}$OC(O)NR$^{10}$—;

$R^{10}$ is independently selected from hydrogen, $C_1$–$C_6$alkyl, benzyl and aryl;
$R^{11}$ is independently selected from $C_1$–$C_6$ alkyl and aryl;
$R^{12}$ is independently selected from hydrogen and $C_1$–$C_6$ alkyl;
$R^{13}$ is independently selected from $C_1$–$C_6$ alkyl;

$A^1$ and $A^2$ are independently selected from: a bond, —CH=CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, or S(O)$_m$;

V is selected from:
a) hydrogen,
b) heterocycle,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl,
provided that V is not hydrogen if $A^1$ is S(O)$_m$ and V is not hydrogen if $A^1$ is a bond, n is 0 and $A^2$ is S(O)$_m$;

W is a heterocycle;
Z is independently H$_2$ or O;
m is 0, 1 or 2;
n is 0, 1, 2, 3 or 4;
p is 0, 1, 2, 3 or 4;
r is 0 to 5, provided that r is 0 when V is hydrogen;
s is 4 or 5; and
u is 0 or 1;
or the pharmaceutically acceptable salts thereof.

In a third embodiment of this invention, the inhibitors of farnesyl transferase are illustrated by the formula III:

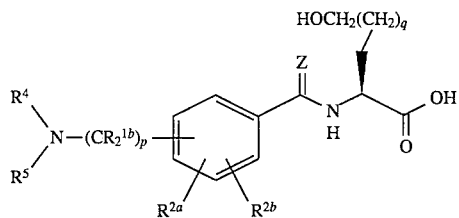

III wherein:
$R^{1a}$ and $R^{1b}$ are independently selected from:
a) hydrogen,
b) aryl, heterocycle, cycloalkyl, alkenyl, alkynyl, R$^{10}$O—, R$^{11}$S(O)$_m$—, R$^{10}$C(O)NR$^{10}$—, CN, NO$_2$,l (R$^{10}$)$_2$N—C(NR$^{10}$)—, R$^{10}$C(O)—, R$^{10}$OC(O)—, N$_3$, —N(R$^{10}$)$_2$, or R$^{11}$OC(O)NR$^{10}$—,
c) $C_1$–$C_6$ alkyl unsubstituted or substituted by aryl, heterocyclic, cycloalkyl, alkenyl, alkynyl, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, N$_3$, —N(R$^{10}$)$_2$, or R$^{11}$OC(O)—NR$^{10}$—;

$R^{2a}$ and $R^{2b}$ are independently selected from:
a) hydrogen,
b) $C_1$–$C_6$ alkyl unsubstituted or substituted by alkenyl, R$^{10}$O—, R$^{11}$S(O)$_m$—, R$^{10}$C(O)NR$^{10}$—, CN, N$_3$, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—,
c) aryl, heterocycle, cycloalkyl, alkenyl, R$^{10}$)—, R$^{11}$S(O)$_m$—, R$^{10}$C(O)NR$^{10}$—, CN, NO$_2$, (R$^{10}$)$_2$N—C(NR$^{10}$)—, R$^{10}$C(O)—, R$^{10}$OC(O)—, N$_3$, —N(R$^{10}$)$_2$, or R$^{11}$OC(O)NR$^{10}$—, and
d) $C_1$–$C_6$ alkyl substituted with an unsubstituted or substituted group selected from aryl, heterocyclic and $C_3$–$C_{10}$ cycloalkyl;

$R^4$ and $R^5$ are independently selected from:
a) hydrogen, and b)

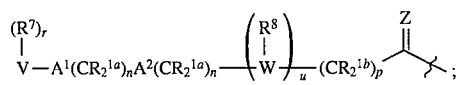

$R^7$ is independently selected from:
a) hydrogen,
b) aryl, heterocycle, cycloalkyl, alkenyl, alkynyl, perfluoroalkyl, F, Cl, Br, R$^{10}$O—, R$^{11}$S(O)$_m$—, R$^{10}$C(O)NR$^{10}$—, CN, NO$_2$, R$^{10}$$_2$N—C(NR$^{10}$)—, R$^{10}$C(O)—, R$^{10}$OC(O)—, N$_3$, —N(R$^{10}$)$_2$, or R$^{11}$OC(O)NR$^{10}$—, and
c) $C_1$–$C_6$ alkyl unsubstituted or substituted by aryl, heterocycle, cycloalkyl, alkenyl, alkynyl, perfluoroalkyl, F, Cl, Br, R$^{10}$O—, R$^{11}$S(O)$_m$—, R$^{10}$C(O)NH—, CN, H$_2$N—C(NH)—, R$^{10}$C(O)—, R$^{10}$OC(O)—, N$_3$, —N(R$^{10}$)$_2$, or R$^{10}$OC(O)NH—;

$R^8$ is selected from:
a) hydrogen,
b) alkenyl, alkynyl, perfluoroalkyl, F, Cl, Br, R$^{10}$O—, R$^{11}$S(O)$_m$—, R$^{10}$C(O)NR$^{10}$—, CN, NO$_2$, (R$^{10}$)$_2$N—C—(NR$^{10}$)—, R$^{10}$C(O)—, R$^{10}$OC(O)—, N$_3$, —N(R$^{10}$)$_2$, or R$^{11}$OC(O)NR$^{10}$—, and
c) $C_1$–$C_6$ alkyl unsubstituted or substituted by perfluoroalkyl, F, Cl, Br, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, N$_3$, —N(R$^{10}$)$_2$, or R$^{11}$OC(O)NR$^{10}$—;

$R^{10}$ is independently selected from hydrogen, $C_1$–$C_6$ alkyl, benzyl and aryl;
$R^{11}$ is independently selected from $C_1$–$C_6$ alkyl and aryl;
$A^1$ and $A^2$ are independently selected from: a bond, —CH=CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, or S(O)$_m$;

V is selected from:
a) hydrogen,
b) heterocycle,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl,
provided that V is not hydrogen if $A^1$ is S(O)$_m$ and V is not hydrogen if $A^1$ is a bond, n is 0 and $A^2$ is S(O)$_m$;

W is a heterocycle;
Z is independently H$_2$ or O;
m is 0, 1 or 2;
n is 0, 1, 2, 3 or 4;
p is 0, 1, 2, 3 or 4;
q is 0, 1 or 2;
r is 0 to 5, provided that r is 0 when V is hydrogen;
s is 4 or 5; and
u is 0or 1;
or the pharmaceutically acceptable salts thereof.

In a fourth embodiment of this invention the prodrugs of compounds of formula III are illustrated by the formula IV:

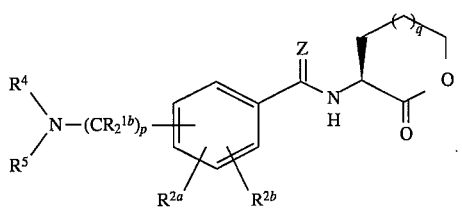

wherein:
$R^{1a}$ and $R^{1b}$ are independently selected from:
a) hydrogen,
b) aryl, heterocycle, cycloalkyl, alkenyl, alkynyl, $R^{10}O-$, $R^{11}S(O)_m-$, $R^{10}C(O)NR^{10}-$, CN, $NO_2$, $(R^{10})_2N-C(NR^{10})-$, $R^{10}C(O)-$, $R^{10}OC(O)-$, $N_3$, $-N(R^{10})_2$, or $R^{11}OC(O)NR^{10}-$,
c) $C_1-C_6$ alkyl unsubstituted or substituted by aryl, heterocyclic, cycloalkyl, alkenyl, alkynyl, $R^{10}O-$, $R^{11}S(O)_m-$, $R^{10}C(O)NR^{10}-$, CN, $(R^{10})_2N-C(NR^{10})-$, $R^{10}C(O)-$, $R^{10}OC(O)-$, $N_3$, $-N(R^{10})_2$, or $R^{11}OC(O)-NR^{10}-$;

$R^{2a}$ and $R^{2b}$ are independently selected from:
a) hydrogen,
b) $C_1-C_6$ alkyl unsubstituted or substituted by alkenyl, $R^{10}O-$, $R^{11}S(O)_m-$, $R^{10}C(O)NR^{10}-$, CN, $N_3$, $(R^{10})_2N-C(NR^{10})-$, $R^{10}C(O)-$, $R^{10}OC(O)-$, $-N(R^{10})_2$, or $R^{11}OC(O)NR^{10}-$,
c) aryl, heterocycle, cycloalkyl, alkenyl, $R^{10}O-$, $R^{11}S(O)_m-$, $R^{10}C(O)NR^{10}-$, CN, $NO_2$, $(R^{10})_2N-C(NR^{10})-$, $R^{10}C(O)-$, $R^{10}OC(O)-$, $N_3$, $-N(R^{10})_2$, or $R^{11}OC(O)NR^{10}-$, and
d) $C_{hd\ 1}-C_6$ alkyl substituted with an unsubstituted or substituted group selected from aryl, heterocyclic and $C_3-C_{10}$ cycloalkyl;

$R^4$ and $R^5$ are independently selected from:
a) hydrogen, and
b)

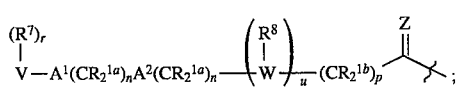

$R^7$ is independently selected from:
a) hydrogen,
b) aryl, heterocycle, cycloalkyl, alkenyl, alkynyl, perfluoroalkyl, F, Cl, Br, $R^{10}O-$, $R^{11}S(O)_m-$, $R^{10}C(O)NR^{10}-$, CN, $NO_2$, $R^{10}_2N-C(NR^{10})-$, $R^{10}C(O)-$, $R^{10}OC(O)-$, $N_3$, $-N(R^{10})_2$, or $R^{11}OC(O)NR^{10}-$, and
c) $C_1-C_6$ alkyl unsubstituted or substituted by aryl, heterocycle, cycloalkyl, alkenyl, alkynyl, perfluoroalkyl, F, Cl, Br, $R^{10}O-$, $R^{11}S(O)_m-$, $R^{10}C(O)NH-$, CN, $H_2N-C(NH)-$, $R^{10}C(O)-$, $R^{10}OC(O)-$, $N_3$, $-N(R^{10})_2$, or $R^{10}OC(O)NH-$;
R8 is selected from:
a) hydrogen,
b) alkenyl, alkynyl, perfluoroalkyl, F, Cl, Br, $R^{10}O-$, $R^{11}S(O)_m-$, $R^{10}C(O)NR^{10}-$, CN, $NO_2$, $(R^{10})_2N-C-(NR^{10})-$, $R^{10}C(O)-$, $R^{10}OC(O)-$, $N_3$, $-N(R^{10})_2$, or $R^{11}OC(O)NR^{10}-$, and
c) $C_1-C_6$ alkyl unsubstituted or substituted by perfluoroalkyl, F, Cl, Br, $R^{10}O-$, $R^{11}S(O)_m-$, $R^{10}C(O)NR^{10}-$, CN, $(R^{10})_2N-C(NR^{10})-$, $R^{10}C(O)-$, $R^{10}OC(O)-$, $N_3$, $-N(R^{10})_2$, or $R^{11}OC(O)NR^{10}-$;

$R^{10}$ is independently selected from hydrogen, $C_1-C_6$ alkyl, benzyl and aryl;
$R^{11}$ is independently selected from $C_1-C_6$ alkyl and aryl;
$A^1$ and $A^2$ are independently selected from: a bond, $-CH=CH-$, $-C\equiv C-$, $-C(O)-$, $-C(O)NR^{10}-$, $-NR^{10}C(O)-$, O, $-N(R^{10})-$, $-S(O)_2N(R^{10})-$, $-N(R^{10})S(O)_2-$, or $S(O)_m$;
V is selected from:
a) hydrogen,
b) heterocycle,
c) aryl,
d) $C_1-C_{20}$ alkyl wherein from 0 to 4 carbon atoms are replaced with a a heteroatom selected from O, S, and N, and
e) $C_2-C_{20}$ alkenyl,
provided that V is not hydrogen if $A^1$ is $S(O)_m$ and V is not hydrogen if $A^1$ is a bond, n is 0 and $A^2$ is $S(O)_m$;
W is a heterocycle;
Z is independently $H_2$ or O;
m is 0, 1 or 2;
n is 0, 1, 2, 3 or 4;
p is 0, 1, 2, 3 or 4;
q is 0, 1 or 2;
r is 0 to 5, provided that r is 0 when V is hydrogen;
s is 4 or 5; and
u is 0or 1;
or the pharmaceutically acceptable salts thereof.

In a more preferred embodiment of this invention, the Ras farnesyl transferase inhibitors are illustrated by the Formula Ia:

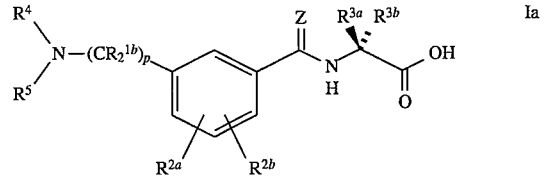

wherein:
$R^{1a}$ is independently selected from: hydrogen or $C_1-C_6$ alkyl;
$R^{1b}$ is independently selected from:
a) hydrogen,
b) aryl, heterocycle, cycloalkyl, $R^{10}O-$, $-N(R^{10})_2$ or alkenyl,
c) $C_1-C_6$ alkyl unsubstituted or substituted by aryl, heterocycle, cycloalkyl, alkenyl, $R^{10}O-$, or $-N(R^{10})_2$;
$R^{2a}$ is selected from:
a) hydrogen,
b) $C_1-C_6$ alkyl unsubstituted or substituted by alkenyl, $R^{10}O-$, $R^{11}S(O)_m-$, $R^{10}C(O)NR^{10}-$, CN, $N_3$, $(R^{10})_2N-C(NR^{10})-$, $R^{10}C(O)-$, $R^{10}OC(O)-$, $-N(R^{10})_2$, or $R^{11}OC(O)NR^{10}-$,
c) aryl, heterocycle, cycloalkyl, alkenyl, $R^{10}O-$, $R^{11}S(O)_m-$, $R^{10}C(O)NR^{10}-$, CN, $NO_2$, $(R^{10})_2N-C(NR^{10})-$, $R^{10}C(O)-$, $R^{10}OC(O)-$, $N_3$, $-N(R^{10})_2$, or $R^{11}OC(O)NR^{10}-$, and
d) $C_1-C_6$ alkyl substituted with an unsubstituted or substituted group selected from aryl, heterocyclic and $C_3-C_{10}$ cycloalkyl;
$R^{2b}$ is hydrogen;
$R^{3a}$ and $R^{3b}$ are independently selected from:
a) a side chain of a naturally occurring amino acid, b) an oxidized form of a side chain of a naturally occurring amino acid which is:
   i) methionine sulfoxide, or
   ii) methionine sulfone,
c) substituted or unsubstituted $C_1$–$C_{10}$ alkyl, $C_2$–$C_{10}$ alkenyl, $C_3$–$C_{10}$ cycloalkyl, aryl or heterocyclic group, wherein the substituent is selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
d) $C_1$–$C_6$ alkyl substituted with an unsubstituted or substituted group selected from aryl, heterocycle and $C_3$–$C_{10}$ cycloalkyl;

$R^4$ and $R^5$ are independently selected from:
a) hydrogen, and
b)

$$\overset{(R^7)_r}{\underset{V-A^1(CR_2^{1a})_nA^2(CR_2^{1a})_n}{|}}-\left(\overset{R^8}{\underset{W}{|}}\right)_u-(CR_2^{1b})_p\overset{Z}{\underset{}{\diagup\!\!\!\diagdown}};$$

$R^7$ is independently selected from:
a) hydrogen,
b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, $R^{10}OC(O)$—, $N(R^{10})_2$, or $R^{11}OC(O)NR^{10}$—, and
c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^8$ is selected from:
a) hydrogen,
b) $C_2$–$C_6$ alkenyl, $C_2$–$C_6$ alkynyl, $C_1$–$C_6$ perfluoroalkyl, F, Cl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—, and
c) $C_1$–$C_6$ alkyl unsubstituted or substituted by $C_1$–$C_6$ perfluoroalkyl, F, Cl, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^{10}$ is independently selected from hydrogen, $C_1$–$C_6$ alkyl, benzyl and aryl;
$R^{11}$ is independently selected from $C_1$–$C_6$ alkyl and aryl;
$A^1$ and $A^2$ are independently selected from: a bond, —CH=CH—, —C≡C—, —C(O)—, —C(O)NR^{10}—, O, —N(R^{10})—, or $S(O)_m$;

V is selected from:
a) hydrogen,
b) heterocycle selected from pyrrolidinyl, imidazolyl, pyridinyl, thiazolyl, pyridonyl, 2-oxopiperidinyl, indolyl, quinolinyl, isoquinolinyl, and thienyl,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, and
provided that V is not hydrogen if $A^1$ is $S(O)_m$ and V is not hydrogen if $A^1$ is a bond, n is 0 and $A^2$ is $S(O)_m$;
W is a heterocycle selected from pyrrolidinyl, imidazolyl, pyridinyl, thiazolyl, pyridonyl, 2-oxopiperidinyl, indolyl, quinolinyl, or isoquinolinyl;
Z is independently $H_2$ or O;

m is 0, 1 or 2;
n is 0, 1, 2, 3 or 4;
p is 0, 1, 2, 3 or 4;
r is 0 to 5, provided that r is 0 when V is hydrogen; and
u is 0 or 1;
or the pharmaceutically acceptable salts thereof.

In a second more preferred embodiment of this invention, the prodrugs of the preferred compounds of Formula I are illustrated by the Formula IIa:

$$\underset{R^5}{\overset{R^4}{\diagdown}}N-(CR_2^{1b})_p-\underset{R^{2a}\ R^{2b}}{\diagdown\!\diagup}-\overset{Z}{\underset{H}{\overset{\|}{C}}}-\underset{O}{\overset{R^{3a}\ R^{3b}}{\underset{}{N}}}-OR^6 \qquad IIa$$

$R^{1a}$ is independently selected from: hydrogen or $C_1$–$C_6$ alkyl;
$R^{1b}$ is independently selected from:
a) hydrogen,
b) aryl, heterocycle, cycloalkyl, $R^{10}O$—, —$N(R^{10})_2$ or alkenyl,
c) $C_1$–$C_6$ alkyl unsubstituted or substituted by aryl, heterocycle, cycloalkyl, alkenyl, $R^{10}O$—, or —$N(R^{10})_2$;

$R^{2a}$ is selected from:
a) hydrogen,
b) $C_1$–$C_6$ alkyl unsubstituted or substituted by alkenyl, $R^{10}O$—, $R^{11}S(O)_m$—, $R^{10}C(O)NR^{10}$—, CN, $N_3$, $(R^{10})_2N$—$C(NR^{10})$—, $R^{10}C(O)$—, $R^{10}OC(O)$—, —$N(R^{10})_2$, or $R^{11}OC(O)NR^{10}$—,
c) aryl, heterocycle, cycloalkyl, alkenyl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—, and
d) $C_1$–$C_6$ alkyl substituted with an unsubstituted or substituted group selected from aryl, heterocyclic and $C_3$–$C_{10}$ cycloalkyl;

$R^{2b}$ is hydrogen;
$R^{3a}$ and $R^{3b}$ are independently selected from:
a) a side chain of a naturally occurring amino acid,
b) an oxidized form of a side chain of a naturally occurring amino acid which is:
   i) methionine sulfoxide, or
   ii) methionine sulfone,
c) substituted or unsubstituted $C_1$–$C_{10}$ alkyl, $C_2$–$C_{10}$ alkenyl, $C_3$–$C_{10}$ cycloalkyl, aryl or heterocyclic group, wherein the substituent is selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
d) $C_1$–$C_6$ alkyl substituted with an unsubstituted or substituted group selected from aryl, heterocycle and $C_3$–$C_{10}$ cycloalkyl;

$R^4$ and $R^5$ are independently selected from:
a) hydrogen, and
b)

$$\overset{(R^7)_r}{\underset{V-A^1(CR_2^{1a})_nA^2(CR_2^{1a})_n}{|}}-\left(\overset{R^8}{\underset{W}{|}}\right)_u-(CR_2^{1b})_p\overset{Z}{\underset{}{\diagup\!\!\!\diagdown}};$$

$R^6$ is
a) substituted or unsubstituted $C_1$–$C_8$ alkyl or substituted or unsubstituted $C_5$–$C_8$ cycloalkyl, wherein the substituent on the alkyl is selected from:

1) aryl,
2) heterocycle,
3) —N(R$^{11}$)$_2$,
4) —OR$^{10}$, or b) 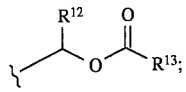

R$^7$ is independently selected from:
a) hydrogen,
b) C$_1$–C$_6$ alkyl, C$_2$–C$_6$ alkenyl, C$_2$–C$_6$ alkyl, C$_1$–C$_6$ perfluoroalkyl, F, Cl, R$^{10}$O—, R$^{10}$C(O)NR$^{10}$—, CN, NO$_2$, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—, and
c) C$_1$–C$_6$ alkyl substituted by C$_1$–C$_6$ perfluoroalkyl, R$^{10}$O—, R$^{10}$C(O)NR$^{10}$—, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—;

R$^8$ is selected from:
a) hydrogen,
b) C$_2$–C$_6$ alkenyl, C$_2$–C$_6$ alkynyl, C$_1$–C$_6$ perfluoroalkyl, F, Cl, R$^{10}$O—, R$^{11}$S(O)$_m$—, R$^{10}$C(O)NR$^{10}$—, CN, NO$_2$, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—, and
c) C$_1$–C$_6$ alkyl unsubstituted or substituted by C$_1$–C$_6$ perfluoroalkyl, F, Cl, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, N(R$^{10}$)$_2$, or R$^{11}$OC(O)NR$^{10}$—;

R$^{10}$ is independently selected from hydrogen, C$_1$–C$_6$ alkyl, benzyl and aryl;
R$^{11}$ is independently selected from C$_1$–C$_6$ alkyl and aryl;
R$^{12}$ is independently selected from hydrogen and C$_1$–C$_6$ alkyl;
R$^{13}$ is independently selected from C$_1$–C$_6$ alkyl;
A$^1$ and A$^2$ are independently selected from: a bond, —CH=CH—, —C≡C—, —C(O)—, —C(O)NR$^{10}$—, O, —N(R$^{10}$)—, or S(O)$_m$;
V is selected from:
a) hydrogen,
b) heterocycle selected from pyrrolidinyl, imidazolyl, pyridinyl, thiazolyl, pyridonyl, 2-oxopiperidinyl, indolyl, quinolinyl, isoquinolinyl, and thienyl,
c) aryl,
d) C$_1$–C$_{20}$ alkyl wherein from 0 to 4 carbon atoms are replaced with a a heteroatom selected from O, S, and N, and
e) C$_2$–C$_{20}$ alkenyl, and
provided that V is not hydrogen if A$^1$ is S(O)$_m$ and V is not hydrogen if A$^1$ is a bond, n is 0 and A$^2$ is S(O)$_m$;
W is a heterocycle selected from pyrrolidinyl, imidazolyl, pyridinyl, thiazolyl, pyridonyl, 2-oxopiperidinyl, indolyl, quinolinyl, or isoquinolinyl;
Z is independently H$_2$ or O;
m is 0, 1 or 2;
n is 0, 1, 2, 3 or 4;
p is 0, 1, 2, 3 or 4;
r is 0 to 5, provided that r is 0 when V is hydrogen; and
u is 0 or 1;
or the pharmaceutically acceptable salts thereof.

In a third more preferred embodiment of this invention, the inhibitors of farnesyl transferase are illustrated by the formula IIIa:

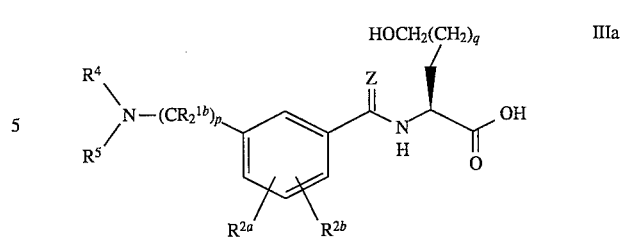

wherein:
R$^{1a}$ is independently selected from: hydrogen or C$_1$–C$_6$ alkyl;
R$^{1b}$ is independently selected from:
a) hydrogen,
b) aryl, heterocycle, cycloalkyl, R$^{10}$O—, —N(R$^{10}$)$_2$ or alkenyl,
c) C$_1$–C$_6$ alkyl unsubstituted or substituted by aryl, heterocycle, cycloalkyl, alkenyl, R$^{10}$O—, or —N(R$^{10}$)$_2$;
R$^{2a}$ is selected from:
a) hydrogen,
b) C$_1$–C$_6$ alkyl unsubstituted or substituted by alkenyl, R$^{10}$O—, R$^{11}$S(O)$_m$—, R$^{10}$C(O)NR$^{10}$—, CN, N$_3$, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—,
c) aryl, heterocycle, cycloalkyl, alkenyl, R$^{10}$O—, R$^{11}$S(O)$_m$—, R$^{10}$C(O)NR$^{10}$—, CN, NO$_2$, (R$^{10}$)$_2$N—C(NR$^{10}$)—, R$^{10}$C(O)—, R$^{10}$OC(O)—, N$_3$, —N(R$^{10}$)$_2$, or R$^{11}$OC(O)NR$^{10}$—, and
d) C$_1$–C$_6$ alkyl substituted with an unsubstituted or substituted group selected from aryl, heterocyclic and C$_3$–C$_{10}$ cycloalkyl;
R$^{2b}$ is hydrogen;
R$^4$ and R$^5$ are independently selected from:
a) hydrogen, and
b)

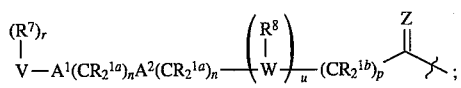

R$^7$ is independently selected from:
a) hydrogen,
b) C$_1$–C$_6$ alkyl, C$_2$–C$_6$ alkenyl, C$_2$–C$_6$ alkynyl, C$_1$–C$_6$ perfluoroalkyl, F, Cl, R$^{10}$O—, R$^{10}$C(O)NR$^{10}$—, CN, NO$_2$, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—, and
c) C$_1$–C$_6$ alkyl substituted by C$_1$–C$_6$ perfluoroalkyl, R$^{10}$O—, R$^{10}$C(O)NR$^{10}$—, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—;

R$^8$ is selected from:
a) hydrogen,
b) C$_2$–C$_6$ alkenyl, C$_2$–C$_6$ alkynyl, C$_1$–C$_6$ perfluoroalkyl, F, Cl, R$^{10}$O—, R$^{11}$S(O)$_m$—, R$^{10}$C(O)NR$^{10}$—, CN, NO$_2$, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—, and
c) C$_1$–C$_6$ alkyl unsubstituted or substituted by C$_1$–C$_6$ perfluoroalkyl, F, Cl, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—;

R$^{10}$ is independently selected from hydrogen, C$_1$–C$_6$ alkyl, benzyl and aryl;
R$^{11}$ is independently selected from C$_1$–C$_6$ alkyl and aryl;

$A^1$ and $A^2$ are independently selected from: a bond, —CH=CH—, —C≡C—, —C(O)—, —C(O)NR$^{10}$—, O, —N(R$^{10}$)—, or S(O)$_m$;

V is selected from:
a) hydrogen,
b) heterocycle selected from pyrrolidinyl, imidazolyl, pyridinyl, thiazolyl, pyridonyl, 2-oxopiperidinyl, indolyl, quinolinyl, isoquinolinyl, and thienyl,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, and provided that V is not hydrogen if $A^1$ is S(O)$_m$ and V is not hydrogen if $A^1$ is a bond, n is 0 and $A^2$ is S(O)$_m$;

W is a heterocycle selected from pyrrolidinyl, imidazolyl, pyridinyl, thiazolyl, pyridonyl, 2-oxopiperidinyl, indolyl, quinolinyl, or isoquinolinyl;

Z is independently $H_2$ or O;
m is 0, 1 or 2;
n is 0, 1, 2, 3 or 4;
p is 0, 1, 2, 3 or 4;
q is 0, 1 or 2;
r is 0 to 5, provided that r is 0 when V is hydrogen; and
u is 0 or 1;

or the pharmaceutically acceptable salts thereof.

In a fourth more preferred embodiment of this invention, the prodrugs of the preferred compounds of Formula III are illustrated by the Formula IVa:

IVa wherein
$R^{1a}$ is independently selected from: hydrogen or $C_1$–$C_6$ alkyl;
$R^{1b}$ is independently selected from:
a) hydrogen,
b) aryl, heterocycle, cycloalkyl, R$^{10}$O—, —N(R$^{10}$)$_2$ or alkenyl,
c) $C_1$–$C_6$ alkyl unsubstituted or substituted by aryl, heterocycle, cycloalkyl, alkenyl, R$^{10}$O—, or —N(R$^{10}$)$_2$;

$R^{2a}$ is selected from:
a) hydrogen,
b) $C_1$–$C_6$ alkyl unsubstituted or substituted by alkenyl, R$^{10}$O—, R$^{11}$S(O)$_m$—, R$^{10}$C(O)NR$^{10}$—, CN, N$_3$, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—,
c) aryl, heterocycle, cycloalkyl, alkenyl, R$^{10}$O—, R$^{11}$S(O)$_m$—, R$^{10}$C(O)NR$^{10}$—, CN, NO$_2$, (R$^{10}$)$_2$N—C(NR$^{10}$)—, R$^{10}$C(O)—, R$^{10}$OC(O)—, N$_3$, —N(R$^{10}$)$_2$, or R$^{11}$OC(O)NR$^{10}$—, and
d) $C_1$–$C_6$ alkyl substituted with an unsubstituted or substituted group selected from aryl, heterocyclic and $C_3$–$C_{10}$ cycloalkyl;

$R^{2b}$ is hydrogen;
$R^4$ and $R^5$ are independently selected from:
a) hydrogen, and
b)

$R^7$ is independently selected from:
a) hydrogen,
b) $C_1$–$C_6$ alkyl, $C_2$–$C_6$ alkenyl, $C_2$–$C_6$ alkynyl, $C_1$–$C_6$ perfluoroalkyl, F, Cl, R$^{10}$O—, R$^{10}$C(O)NR$^{10}$—, CN, NO$_2$, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—, and
c) $C_1$–$C_6$ alkyl substituted by $C_1$–$C_6$ perfluoroalkyl, R$^{10}$O—, R$^{10}$C(O)NR$^{10}$—, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—;

$R^8$ is selected from:
a) hydrogen,
b) $C_2$–$C_6$ alkenyl, $C_2$–$C_6$ alkynyl, $C_1$–$C_6$ perfluoroalkyl, F, Cl, R$^{10}$O—, R$^{11}$S(O)$_m$—, R$^{10}$C(O)NR$^{10}$—, CN, NO$_2$, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—, and
c) $C_1$–$C_6$ alkyl unsubstituted or substituted by $C_1$–$C_6$ perfluoroalkyl, F, Cl, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—;

$R^{10}$ is independently selected from hydrogen, $C_1$–$C_6$ alkyl, benzyl and aryl;
$R^{11}$ is independently selected from $C_1$–$C_6$ alkyl and aryl;
$A^1$ and $A^2$ are independently selected from: a bond, —CH=CH—, —C≡C—, —C(O)—, —C(O)NR$^{10}$—, O, —N(R$^{10}$)—, or S(O)$_m$;

V is selected from:
a) hydrogen,
b) heterocycle selected from pyrrolidinyl, imidazolyl, pyridinyl, thiazolyl, pyridonyl, 2-oxopiperidinyl, indolyl, quinolinyl, isoquinolinyl, and thienyl,
c) aryl,
d) $C_1$–$C_{20}$ alkyl wherein from 0 to 4 carbon atoms are replaced with a a heteroatom selected from O, S, and N, and e) $C_2$–$C_{20}$ alkenyl, and provided that V is not hydrogen if $A^1$ is S(O)$_m$ and V is not hydrogen if $A^1$ is a bond, n is 0 and $A^2$ is S(O)$_m$;

W is a heterocycle selected from pyrrolidinyl, imidazolyl, pyridinyl, thiazolyl, pyridonyl, 2-oxopiperidinyl, indolyl, quinolinyl, or isoquinolinyl;

Z is independently $H_2$ or O;
m is 0, 1 or 2;
n is 0, 1, 2, 3 or 4;
p is 0, 1, 2, 3 or 4;
q is 0, 1 or 2;
r is 0 to 5, provided that r is 0 when V is hydrogen; and
u is 0 or 1;

or the pharmaceutically acceptable salts thereof.

The preferred compounds of this invention are as follows:

N-(1(S)-carboxy-3-methylthiopropyl)-3-(4-imidazolylmethyl)aminomethylbenzamide

N-(1(S)-carbomethoxy-3-methylthiopropyl)-3-(4-imidazolylmethyl)aminomethylbenzamide N-(1(S)-carboxy-3-methylthiopropyl)-3-[N,N-bis-(4-imidazolemethyl)aminomethyl]benzamide N-(1(S)-carbomethoxy-3-methylthiopropyl)-3-[N,N-bis-(4-imidazolemethyl)aminomethyl]benzamide N-(1(S)-carboxy-3-methylthiopropyl) 3-[(4-imidazolylmethyl)-N-methylaminomethyl]benzamide N-(1(S)-carbomethoxy-3-methylthiopropyl) 3-[(4-imidazolylmethyl)-N-methylaminomethyl]benzamide
N-(1(S)-carboxy-3-methylthiopropyl) 4-[(4-imidazolylmethyl)amino]benzamide
N-(1(S)-carbomethoxy-3-methylthiopropyl) 4-[(4-imidazolylmethyl)amino]benzamide
N-(1(S)-carboxy-3-methylthiopropyl)-3-[(4-imidazolylmethyl) amino]benzamide
N-(1(S)-carbomethoxy-3-methylthiopropyl)-3-[(4-imidazolylmethyl) amino]benzamide
N-(1(S)-carbomethoxy-3-methylthiopropyl)-3-[(4-imidazolylpropyl) amino]benzamide
N-(1(S)-Carboxy-3-methylthiopropyl)-3-[(4-imidazolylpropyl) amino]benzamide
N-(1(S)-Carbomethoxy-3-methylthiopropyl)-3-[N-(4-imidazolylymethyl)-N-(4-nitrobenzyl)aminomethyl]benzamide
N-(1(S)—Carboxy-3-methylthiopropyl)-3-[N-(4-imidazolylymethyl)-N-(4-nitrobenzyl)aminomethyl ]benzamide
N-(1(S)-carboxy-3-methylthiopropyl)-3-[N ,N- bis-(4-nitrophenylmethyl)]aminomethylbenzamide
N-(1(S)-carbomethoxy-3-methylthiopropyl)-3-[N,N-bis-(4-nitrophenylmethyl)aminomethyl]benzamide
or the pharmaceutically acceptable salts thereof.

Specific examples of the compounds of the invention are:

N-(1(S)-carboxy-3-methylthiopropyl)-3-[N,N-bis-(4-nitrophenylmethyl)aminomethyl]benzamide

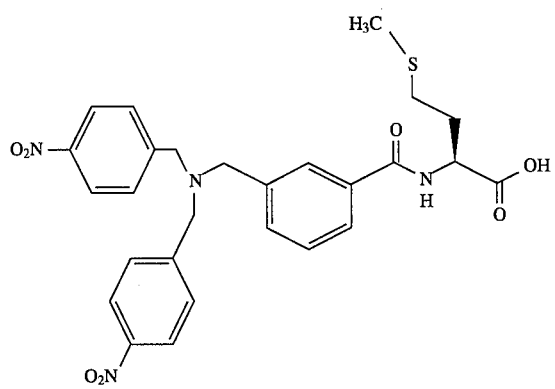

N-(1(S)-carbomethoxy-3-methylthiopropyl)-3-[N,N-bis-(4-nitrophenylmethyl)aminomethyl]benzamide

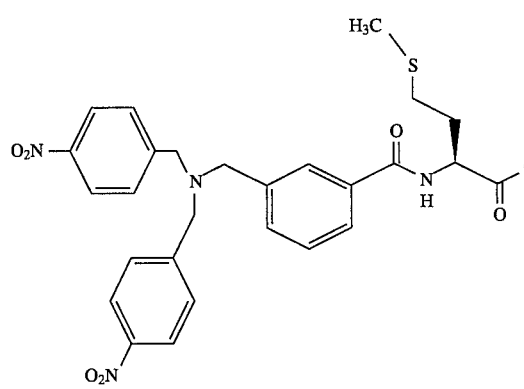

N-(1(S)-carboxy-3-methylthiopropyl)-3-[N,N-bis(4-imidazolemethyl)aminomethyl]benzamide

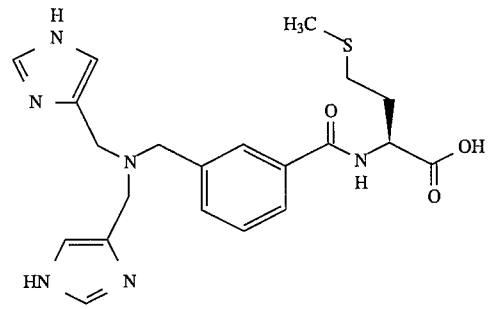

N-(1(S)-carboxymethoxy-3-methylthiopropyl)-3-[N,N-bis(4-imidazolemethyl)aminomethyl]benzamide

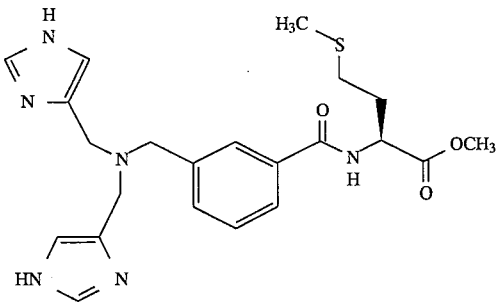

N-(1(S)-Carboxy-3-methylthiopropyl)-3-[N-(4-imidazolylmethyl)-N-(4-nitrobenzyl)aminomethyl]benzamide

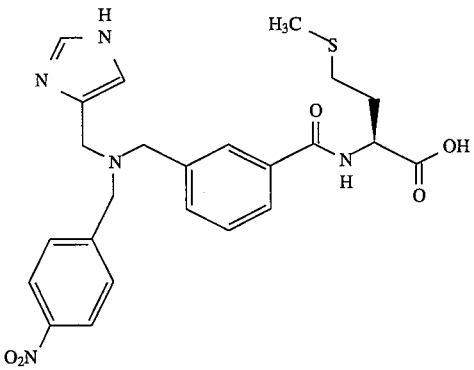

N-(1(S)-Carbomethoxy-3-methylthiopropyl)-3-[N-(4-imidazolylmethyl)-N-(4-nitrobenzyl)aminomethyl]benzamide

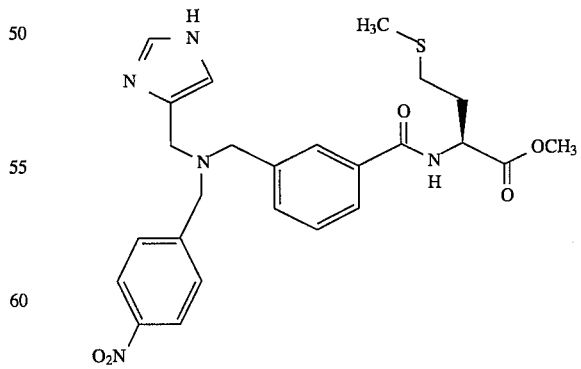

or the pharmaceutically acceptable salts thereof.

In the present invention, the amino acids which are disclosed are identified both by conventional 3 letter and single letter abbreviations as indicated below:

| | | |
|---|---|---|
| Alanine | Ala | A |
| Arginine | Arg | R |
| Asparagine | Asn | N |
| Aspartic acid | Asp | D |
| Asparagine or Aspartic acid | Asx | B |
| Cysteine | Cys | C |
| Glutamine | Gln | Q |
| Glutamic acid | Glu | E |
| Glutamine or Glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The compounds of the present invention may have asymmetric centers and occur as racemates, racemic mixtures, and as individual diastereomers, with all possible isomers, including optical isomers, being included in the present invention.

As used herein, "alkyl" is intended to include both branched and straight-chain saturated aliphatic hydrocarbon groups having the specified number of carbon atoms.

As used herein, "cycloalkyl" is intended to include non-aromatic cyclic hydrocarbon groups having the specified number of carbon atoms. Examples of cycloalkyl groups include cyclopropyl, cyclobutyl, cyclopentyl, cyclohexyl and the like.

"Alkenyl" groups include those groups having the specified number of carbon atoms and having one or several double bonds. Examples of alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl, isoprenyl, farnesyl, geranyl, geranylgeranyl and the like.

As used herein, "aryl" is intended to include any stable monocyclic, bicyclic or tricyclic carbon ring(s) of up to 7 members in each ring, wherein at least one ring is aromatic. Examples of aryl groups include phenyl, naphthyl, anthracenyl, biphenyl, tetrahydronaphthyl, indanyl, phenanthrenyl and the like.

The term heterocycle or heterocyclic, as used herein, represents a stable 5- to 7-membered monocyclic or stable 8- to 11-membered bicyclic or stable 11–15 membered tricyclic heterocycle ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothio-pyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperidinyl, 2-oxopyrrolidinyl, piperidyl, piperazinyl, pyridyl, pyridyl N-oxide, pyridonyl, pyrazinyl, pyrazolidinyl, pyrazolyl, pyrimidinyl, pyrrolidinyl, pyrrolyl, quinazolinyl, quinolinyl, quinolinyl N-oxide, quinoxalinyl, tetrahydrofuryl, tetrahydroisoquinolinyl, tetrahydro-quinolinyl, thiamorpholinyl, thiamorpholinyl sulfoxide, thiazolyl, thiazolinyl, thienofuryl, thienothienyl, and thienyl.

As used herein, the terms "substituted aryl", "substituted heterocycle" and "substituted cycloalkyl" are intended to include the cyclic group which is substituted with 1 or 2 substitutents selected from the group which includes but is not limited to F, Cl, Br, $CF_3$, $NH_2$, $N(C_1-C_6\ alkyl)_2$, $NO_2$, CN, $(C_1-C_6\ alkyl)O$—, —OH, $(C_1-C_6\ alkyl)S(O)_m$—, $(C_1-C_6\ alkyl)C(O)NH$—, $H_2N$—C(NH)—, $(C_1-C_6\ alkyl)C(O)$—, $(C_1-C_6\ alkyl)OC(O)$—, $N_3$, $(C_1-C_6\ alkyl)OC(O)NH$— and $C_1-C_{20}$ alkyl. When $R^{3a}$ and $R^{3b}$ are combined to form —$(CH_2)_s$—, cyclic moieties are formed. Examples of such cyclic moieties include, but are not limited to:

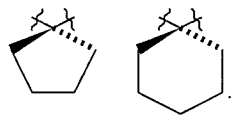

In addition, such cyclic moieties may optionally include a heteroatom(s). Examples of such heteroatom-containing cyclic moieties include, but are not limited to:

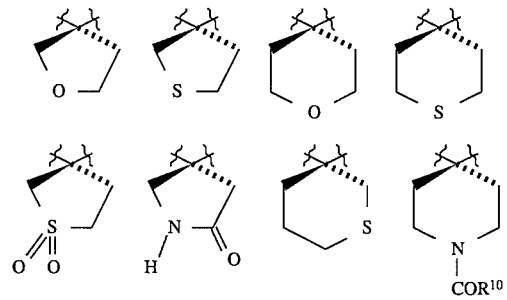

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

It is intended that the definition of any substituent or variable (e.g., $R^{10}$, Z, n, etc.) at a particular location in a molecule be independent of its definitions elsewhere in that molecule. Thus, —$N(R^{10})_2$ represents —NHH, —$NHCH_3$, —$NHC_2H_5$, etc. It is understood that substituents and substitution patterns on the compounds of the instant invention can be selected by one of ordinary skill in the art to provide compounds that are chemically stable and that can be readily synthesized by techniques known in the art as well as those methods set forth below.

The pharmaceutically acceptable salts of the compounds of this invention can be synthesized from the compounds of this invention which contain a basic moiety by conventional chemical methods. Generally, the salts are prepared by reacting the free base with stoichiometric amounts or with an excess of the desired salt-forming inorganic or organic acid in a suitable solvent or various combinations of solvents.

The compounds of the invention can be synthesized from their constituent amino acids by conventional peptide synthesis techniques, and the additional methods described below. Standard methods of peptide synthesis are disclosed, for example, in the following works: Schroeder et at., "The Peptides", Vol. I, Academic Press 1965, or Bodanszky et at., "Peptide Synthesis", Interscience Publishers, 1966, or McOmie (ed.) "Protective Groups in Organic Chemistry", Plenum Press, 1973, or Barany et al., "The Peptides: Analysis, Synthesis, Biology" 2, Chapter 1, Academic Press, 1980, or Stewart et al., "Solid Phase Peptide Synthesis", Second Edition, Pierce Chemical Company, 1984. The teachings of these works are hereby incorporated by reference.

Abbreviations used in the description of the chemistry and in the Examples that follow are:

| | |
|---|---|
| $Ac_2O$ | Acetic anhydride; |
| Boc | t-Butoxycarbonyl; |
| DBU | 1,8-diazabicyclo[5.4.0]undec-7-ene; |
| DMAP | 4-Dimethylaminopyridine; |
| DME | 1,2-Dimethoxyethane; |
| DMF | Dimethylformamide; |
| EDC | 1-(3-dimethylaminopropyl)-3-ethyl-carbodiimidehydrochloride; |
| HOBT | 1-Hydroxybenzotriazole hydrate; |
| $Et_3N$ | Triethylamine; |
| EtOAc | Ethyl acetate; |
| FAB | Fast atom bombardment; |
| HOOBT | 3-Hydroxy-1,2,2-benzotriazin-4(3H)-one; |
| HPLC | High-performance liquid chromatography; |
| MCPBA | m-Chloroperoxybenzoic acid; |
| MsCl | Methanesulfonyl chloride; |
| NaHMDS | Sodium bis(trimethylsilyl)amide; |
| Py | Pyridine; |
| TFA | Trifluoroacetic acid; |
| THF | Tetrahydrofuran. |

Compounds of this invention are prepared by employing the reactions shown in the following Reaction Schemes A–J, in addition to other standard manipulations such as ester hydrolysis, cleavage of protecting groups, etc., as may be known in the literature or exemplified in the experimental procedures. Some key bond-forming and peptide modifying reactions are:

Reaction A Amide bond formation and subsequenmt generation of the amino methyl moiety using standard solution or solid phase methodologies.

Reaction B Preparation of a reduced peptide subunit by reductive alkylation of an amine by an aldehyde using sodium cyanoborohydride or other reducing agents.

Reaction C Alkylation of the amino moiety of the central phenyl ring.

Reaction D Peptide bond formation and protecting group cleavage using standard solution or solid phase methodologies.

These reactions may be employed in a linear sequence to provide the compounds of the invention or they may be used to synthesize fragments which are subsequently joined by the alkylation reactions described in the Reaction Schemes.

REACTION SCHEME A
Reaction A.
Coupling of residues to form an amide bond

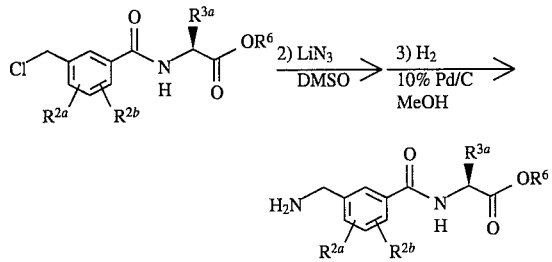

REACTION SCHEME B
Reaction B.
Preparation of reduced amino acid linkages by reductive alkylation

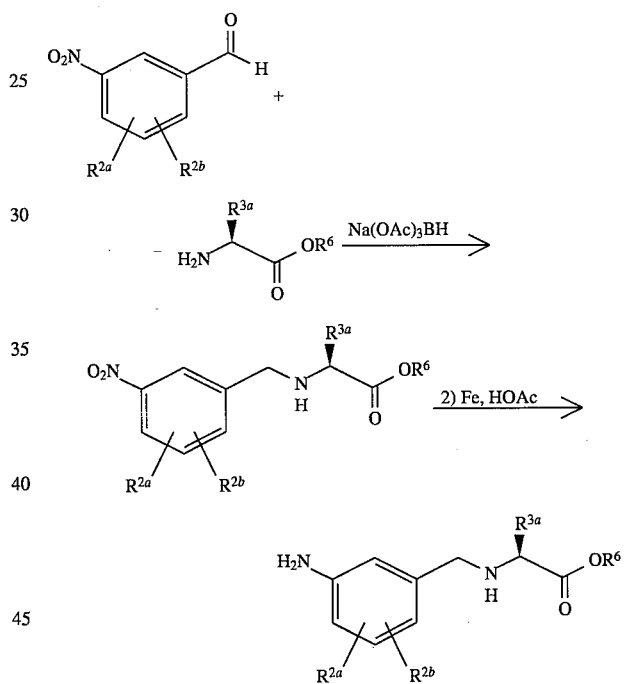

REACTION SCHEME C
Reaction C.
Alkylation of the amino moiety

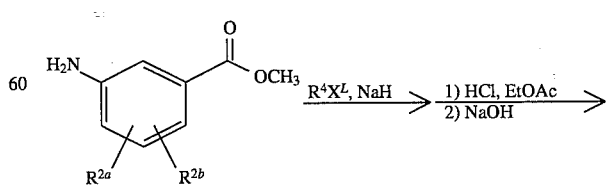

23
-continued
REACTION SCHEME C
Reaction C.
Alkylation of the amino moiety

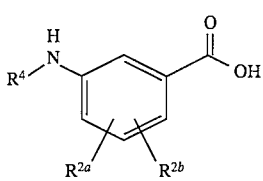

REACTION SCHEME D
Reaction D.
Coupling of residues to form an amide bond

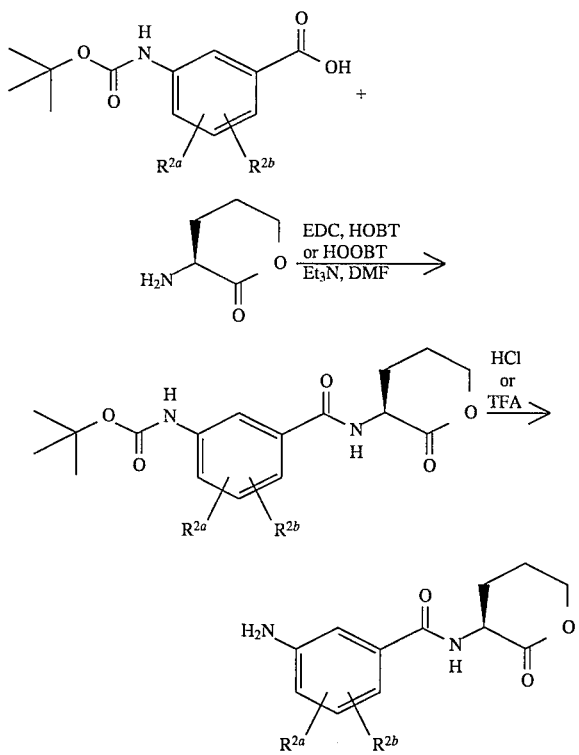

where $X^L$ is a leaving group, e.g., Br—, I— or MsO—;.

Reaction Schemes E–M illustrate reactions wherein the non-sulfhydryl-containing moiety at the N-terminus of the compounds of the instant invention is attached to an aminomethylbenzamide subunit which may be further elaborated to provide the instant compounds. These reactions may be employed in a linear sequence to provide the compounds of the invention or they may be used to synthesize fragments which are subsequently joined by the reactions described in Reaction Schemes A–D.

The intermediates whose synthesis are illustrated in Reaction Schemes A–D can be reductively alkylated with a variety of aldehydes, such as I, as shown in Reaction Scheme E. The aldehydes can be prepared by standard procedures, such as that described by O. P. Goel, U. Krolls, M. Stier and S. Kesten in Organic Syntheses, 1988, 67, 69–75, from the appropriate amino acid (Reaction Scheme E). The reductive alkylation can be accomplished at pH 5–7 with a variety of reducing agents, such as sodium triacetoxyborohydride or sodium cyanoborohydride in a solvent such as dichloroethane, methanol or dimethylformamide. The product II can be deprotected to give the final compounds III with trifluoroacetic acid in methylene chloride. The final

24 product III is isolated in the salt form, for example, as a trifluoroacetate, hydrochloride or acetate salt, among others. The product diamine III can further be selectively protected to obtain IV, which can subsequently be reductively alkylated with a second aldehyde to obtain V. Removal of the protecting group, and conversion to cyclized products such as the dihydroimidazole VII can be accomplished by literature procedures.

Alternatively, the aminomethylbenzamide subunit can be reductively alkylated with other aldehydes such as 1-trityl-4-carboxaldehyde or 1-trityl-4-imidazolylacetaldehyde, to give products such as VIII (Reaction Scheme F). The trityl protecting group can be removed from VIII to give IX, or alternatively, VIII can first be treated with an alkyl halide then subsequently deprotected to give the alkylated imidazole X. Alternatively, the aminomethylbenzamide subunit can be acylated or sulfonylated by standard techniques.

The imidazole acetic acid XI can be converted to the acetate XIII by standard procedures, and XIII can be first reacted with an alkyl halide, then treated with refluxing methanol to provide the regiospecifically alkylated imidazole acetic acid ester XIV. Hydrolysis and reaction with the aminomethylbenzamide subunit in the presence of condensing reagents such as 1-(3-dimethylaminopropyl)-3-ethylcarbodiimide (EDC) leads to acylated products such as XV.

If the aminomethylbenzamide subunit is reductively alkylated with an aldehyde which also has a protected hydroxyl group, such as XVI in Reaction Scheme H, the protecting groups can be subsequently removed to unmask the hydroxyl group (Reaction Schemes H, I). The alcohol can be oxidized under standard conditions to e.g. an aldehyde, which can then be reacted with a variety of organometallic reagents such as Grignard reagents, to obtain secondary alcohols such as XX. In addition, the fully deprotected amino alcohol XXI can be reductively alkylated (under conditions described previously) with a variety of aldehydes to obtain secondary amines, such as XXII (Reaction Scheme J), or tertiary amines.

The Boc protected amino alcohol XVIII can also be utilized to synthesize 2-aziridinylmethylpiperazines such as XXIII (Reaction Scheme K). Treating XVIII with 1,1'-sulfonyldiimidazole and sodium hydride in a solvent such as dimethylformamide led to the formation of aziridine XXIII. The aziridine reacted in the presence of a nucleophile, such as a thiol, in the presence of base to yield the ring-opened product XXIV.

In addition, the aminomethylbenzamide subunit can be reacted with aldehydes derived from amino acids such as O-alkylated tyrosines, according to standard procedures, to obtain compounds such as XXX, as shown in Reaction Scheme L. When R' is an aryl group, XXX can first be hydrogenated to unmask the phenol, and the amine group deprotected with acid to produce XXXI. Alternatively, the amine protecting group in XXX can be removed, and O-alkylated phenolic amines such as XXXII produced.

Reaction Scheme M illustrates a one pot synthesis of an instant compound wherein the N-terminus nitrogen is substituted with two different non-sulfhydryl-containing moieties. Thus, the aminomethylbenzamide subunit is treated with one equivalent of an appropriate aldehyde and, after the reductive adduct has been formed, the in situ intermediate is treated with an equivalent of a different aldehyde.

Similar procedures as are illustrated in Reaction Schemes EM may be employed using other intermediates such as those whose synthesis is illustrated in Reaction Schemes B–D.

5,578,629
SCHEME E
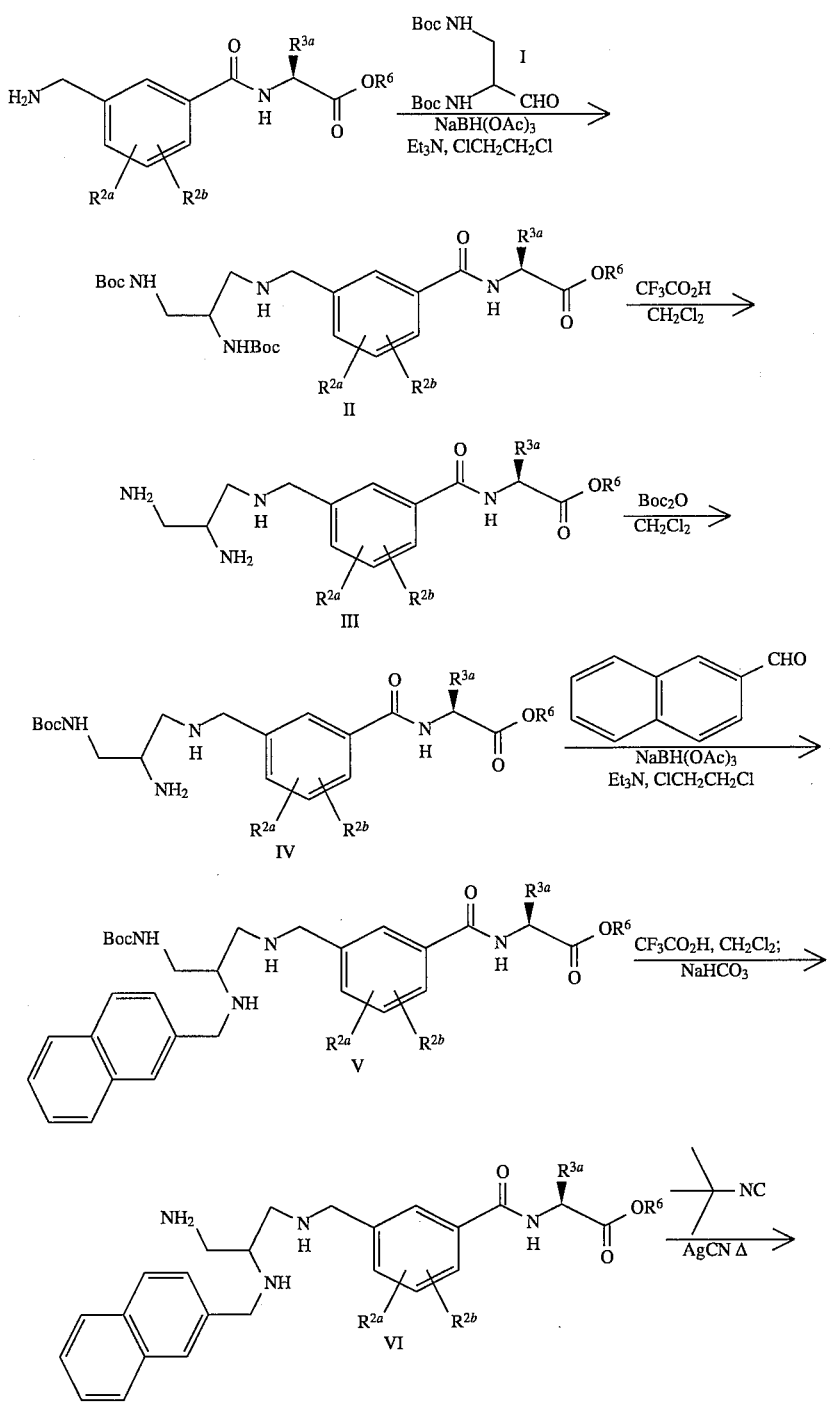

-continued
SCHEME E
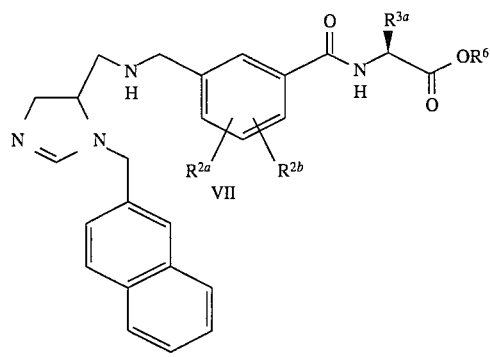
SCHEME F
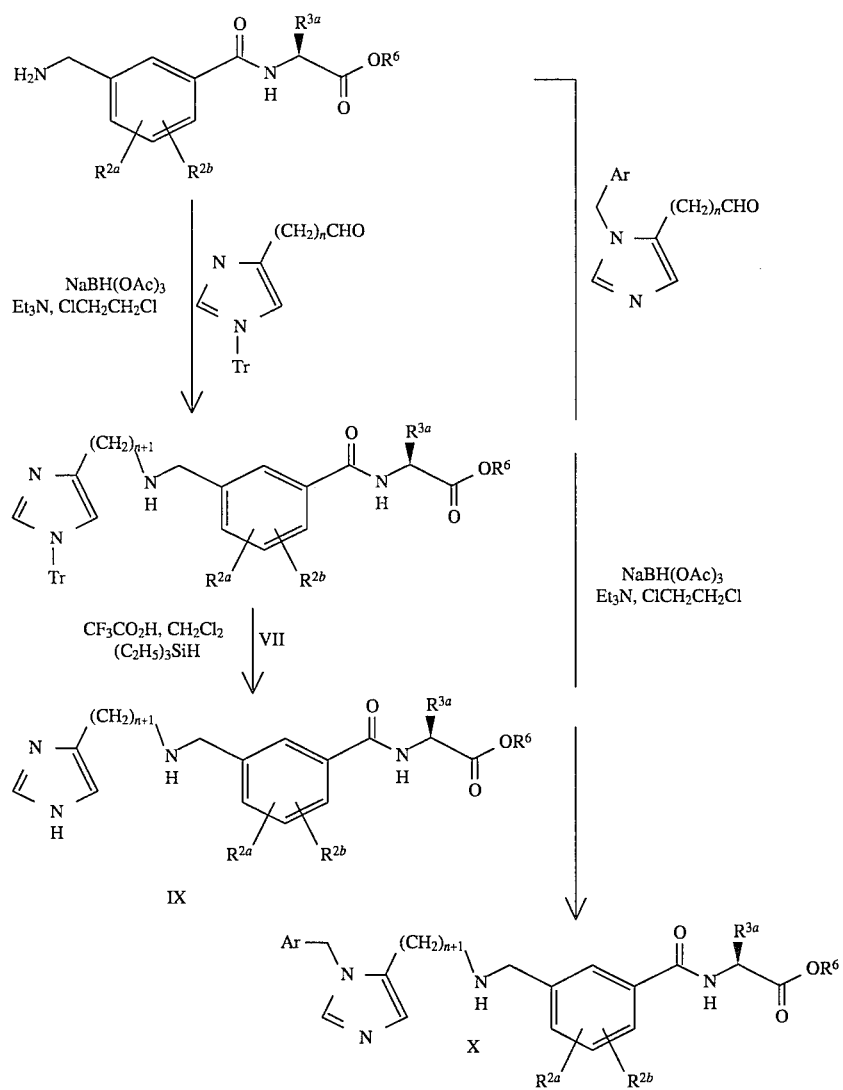

SCHEME G
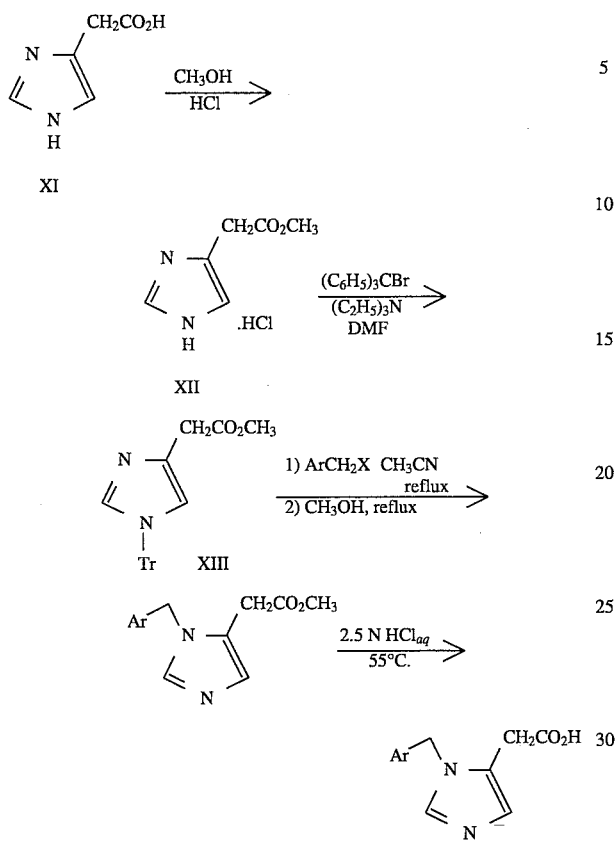
SCHEME H
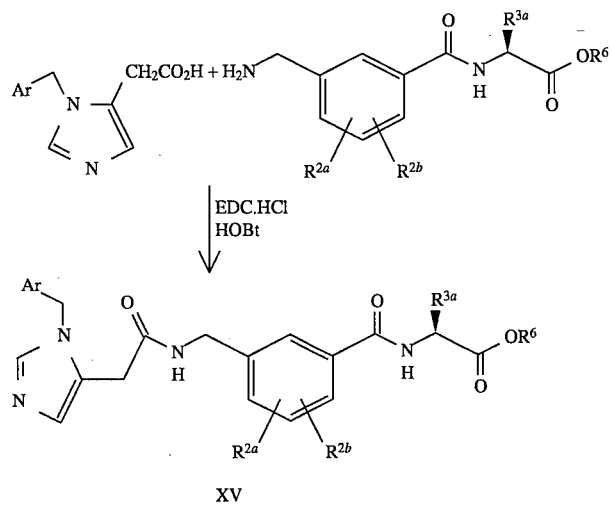

SCHEME I
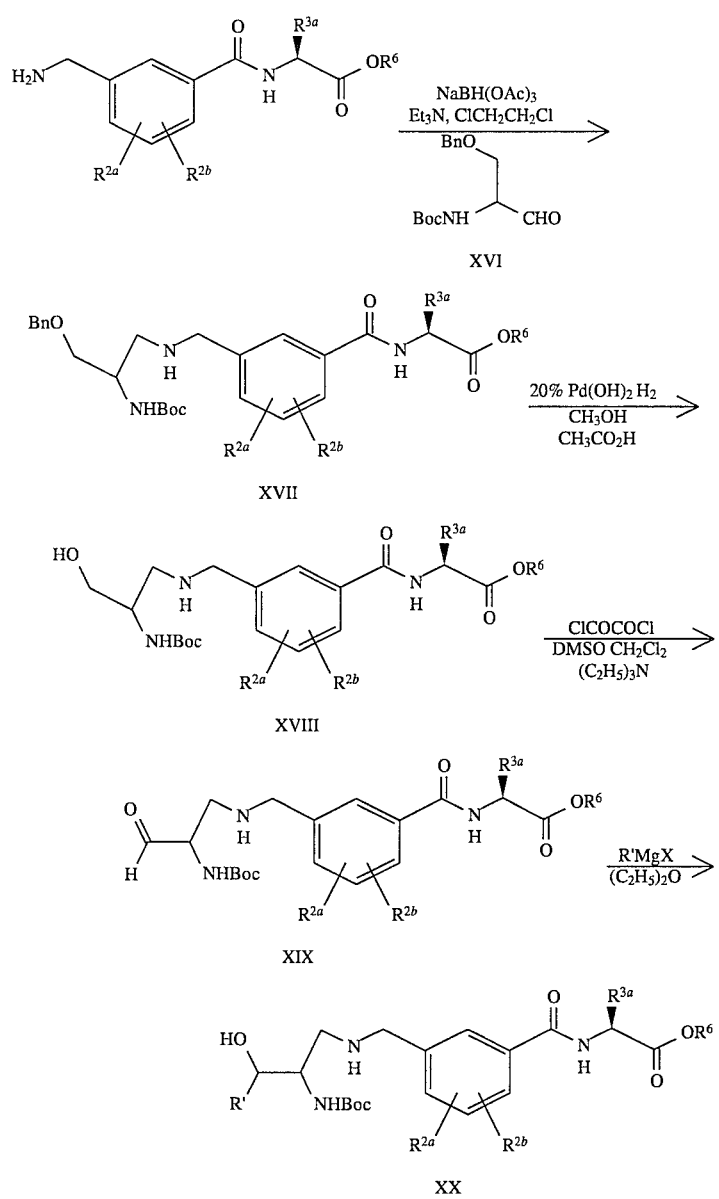
SCHEME J
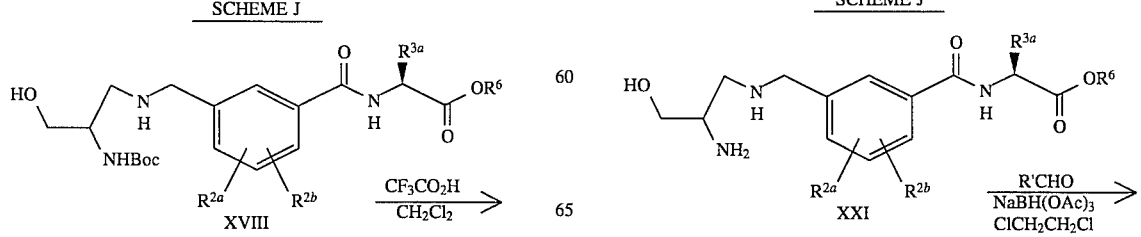

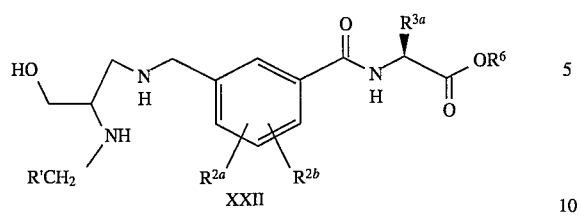
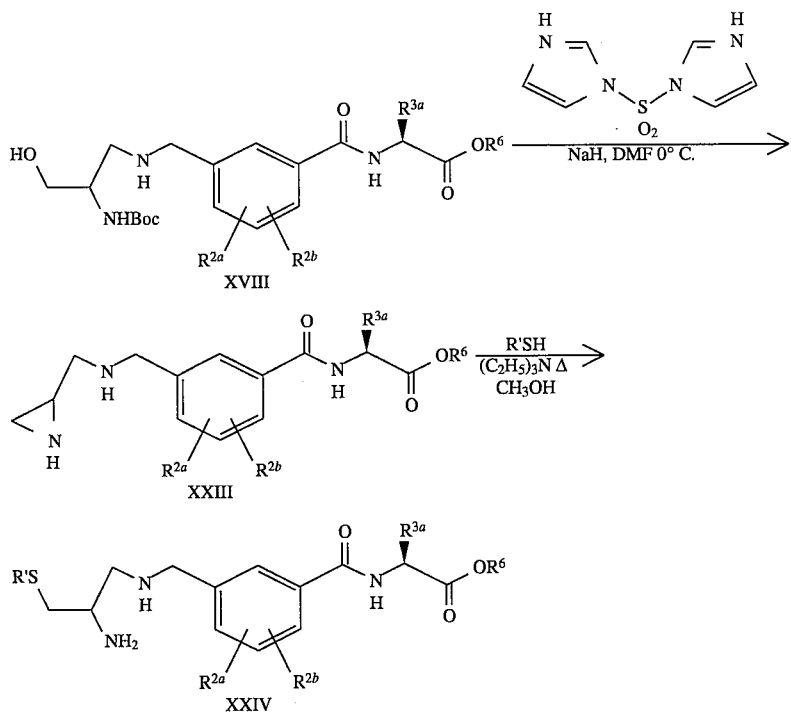
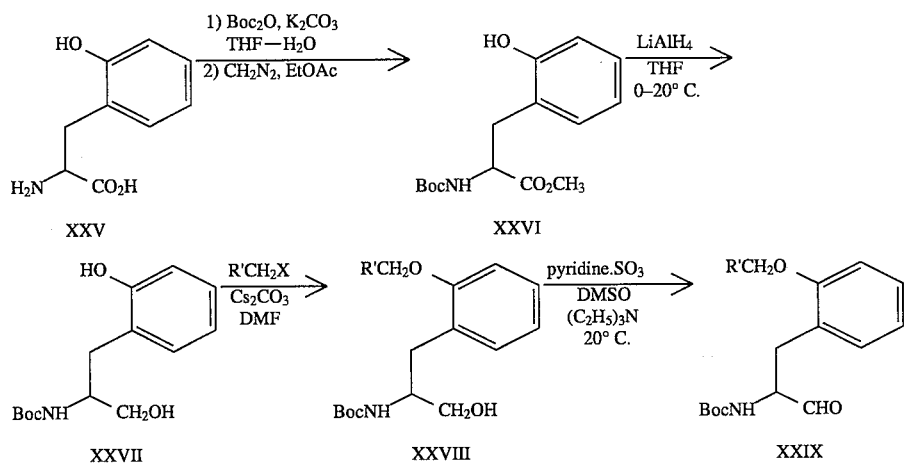

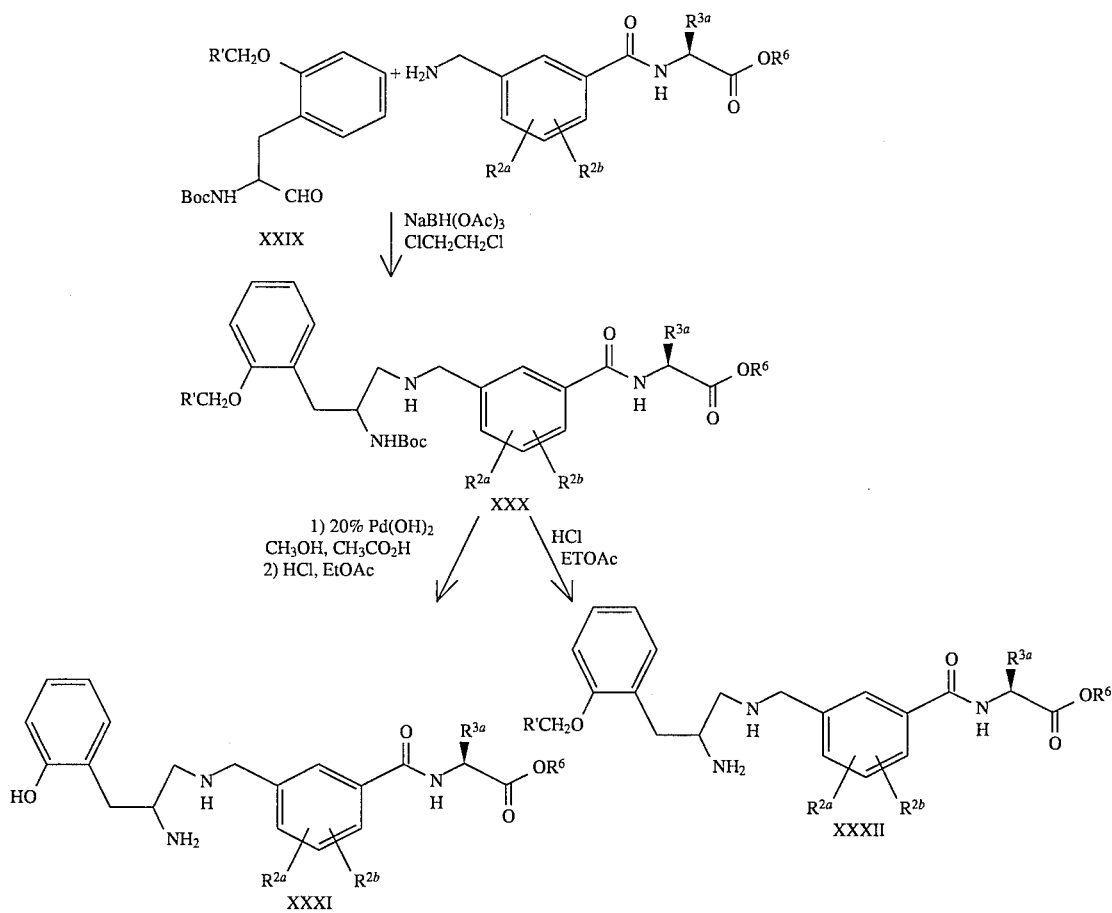

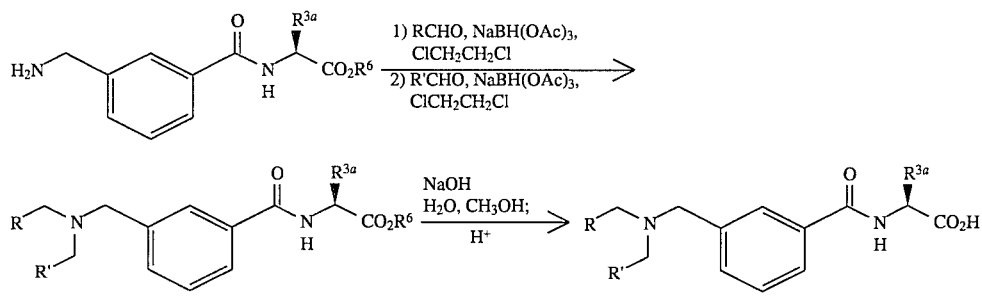

The —NR[4]R[5] moiety of the compounds of the instant invention may provide advantages over a cysteinyl moiety that is incorporated in other types of molecules that are known to be inhibitors of farnesyl protein transferase. In particular, modification of the benzodiazepine compounds described in published PCT application WO 94/26723 with the such —NR[4]R[5] substituents as described herein will provide inhibitors of farnesyl protein transferase of the following formulae A and B:

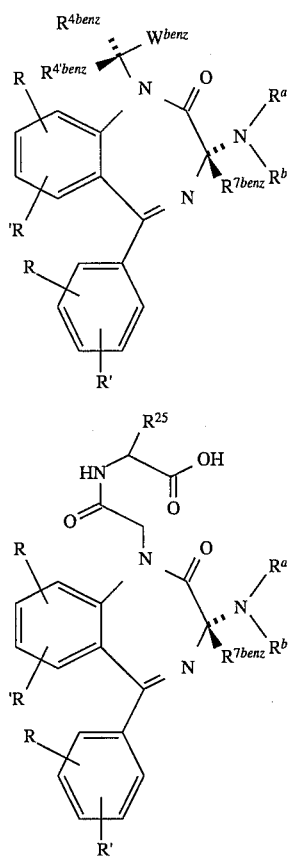

wherein the substituents R, R' and $R^{25}$ are as defined in WO 94/26723, $R^{4benz}$, $R^{4'benz}$, $R^{7benz}$ and $W^{benz}$ are $R^4$, $R^{4'}$, $R^7$ and W respectively as defined in WO 94/26723 and $R^a$ and $R^b$ are defined as $R^4$ and R5 are defined herein respectively.

Preferably, the following combinations of $R^a$ and $R^b$ are selected for incorporation into the compounds of formulae A and B:

| $R^a$ | $R^b$ |
|---|---|
| imidazol-4-ylacetyl | H |
| imidazol-4-ylmethyl | imidazol-4-ylmethyl |
| 4-nitrobenzyl | imidazol-4-ylmethyl |
| 3-(4-cyanobenzyl)-imidazol-4-acetyl | H |
| 3-(4-cyanobenzyl)-imidazol-4-acetyl | $CH_3$ |

Most preferably, the benzodiazepine compound would be selected from the following formulae:

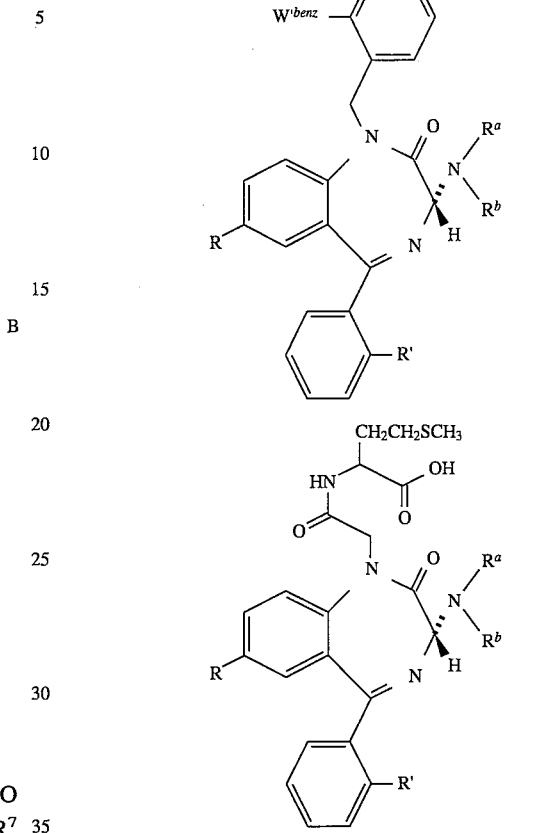

wherein R and R' are as defined in WO 94/26723 and $W^{'benz}$ is W' as defined in WO 94/26723 and $R^a$ and $R^b$ are defined as $R^4$ and $R^5$ are defined herein respectively.

Such benzodiazepine analogs may be synthesized by techniques well known in the art, as well as procedures outlined in WO 94/26723. General methods of synthesis of the benzediazapine analogs of this invention are shown in Schemes N, P and Q. Typically a convergent route is employed, which joins the key intermediate 9 (Scheme N) with suitably functionalized amine and $R^a$ and $R^b$ components (Schemes P and Q) using standard amide bond-forming procedures.

As shown in Scheme N, the protected amino acid 9 may be prepared from a suitably substituted 2-aminobenzophenone (1). Many 2-aminobenzophenones are known in the art or are available form commercial sources such as Aldrich Chemical Co. General methods for the synthesis of new 2-aminobenzophenones may be found in the literature (c.f. Walsh, D. A. Synthesis, 677–688 (1980).

Acylation of 1 with a haloacetyl halide, such as bromoacetyl bromide in a suitable solvent mixture, such as water/$CH_2Cl_2$, typically at temperatures ranging from 0° C. to 24° C., produces amide 2. Reaction of 2 with ammonia in a polar solvent such as methanol at 25° to 75° C. then gives the 1,4-benzodiazepin-2-one 3, after evaporation of the solvent. Alkylation of 3 with a substituted organic ester (4), preferably tert-butyl bromacetate, in the presence of a base, preferably $Cs_2CO_3$ in 1-methyl-2-pyrrolidinone at ambient temperature, gives 5. Alternatively, 3 may be alkylated at N-1 with a variety of other alkylating agents, for instance, esters of substituted or unsubstituted acrylates, 4-bromobutanoates, etc. Branched compounds (i.e. $R^{4benz}$ and/or $R^{4'benz}$ ≠H), may be prepared by generation of the polyanion of 5 with base and alkylation with an appropriate alkyl halide. Subsequent to alkylation, the ester of 5 may be cleaved with an acid such as TFA (for the tert-butyl esters) or under mild aqueous base hydrolysis (for other alkyl esters) at temperatures between 0° and 25 ° C.

The acid 6 is converted to amino acid 8 via reaction of the dianion, generated with at least two equivalents of a strong base with an electrophilic aminating agent. Alternatively, 6 may be halogenated and reacted with an amine source such as azide (followed by reduction) or ammonia. Preferably, 6 is reacted with 4 equivalents of potassium tert-butoxide in glyme at –5 ° C. for 30 min and treated with 1.1 equivalents of isobutyl nitrite. The resulting oxime 7 can then be reduced to the racemic amino acid 8 using a variety of reductants, preferably hydrogenation at 40 psig in the presence of Ruthenium on carbon or Raney nickel in methanol at 50° to 70 ° C. for 1–4 days.

Amino acid 8 is then suitably protected for selective coupling at the carboxyl terminus. For example, 8 can be converted to the N-BOC derivative 9 using standard amino acid protection conditions, preferably, reaction with equimolar amounts of di-tert-butyl dicarbonate and triethyl amine in DMF/water at ambient temperature.

For compounds where $R^a$≠H, 9 can be alkylated at nitrogen with a wide variety of alkylating agents including n-alkyl, branched alkyl, and benzyl, according to the standard procedure of Benoiton, et al., Can. J. Chem. 1977, 55, 906. For example, reaction of 9 with at least 2 equivalents of base and an alkylating agent in a polar, aprotic solvent at 0° to 50 ° C. for 0.5 to 48 h give 10. Also, the reactions shown in Schemes E–M may be utilized with the compound 9.

SCHEME N

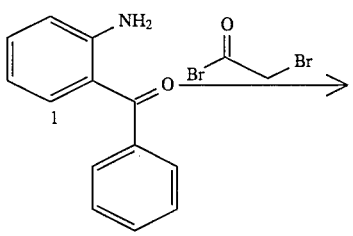

-continued
SCHEME N

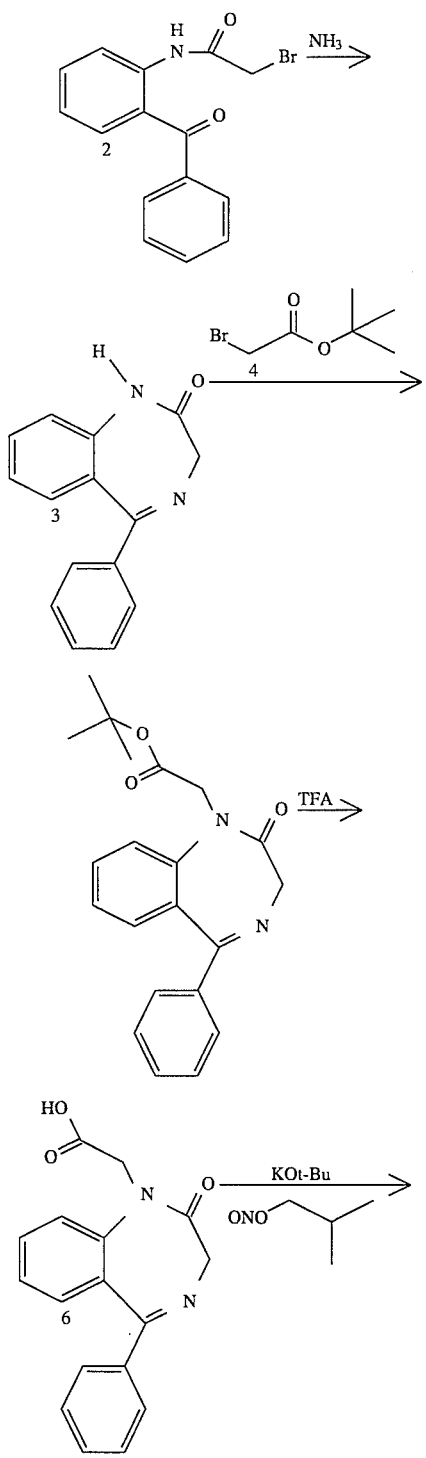

-continued
SCHEME N

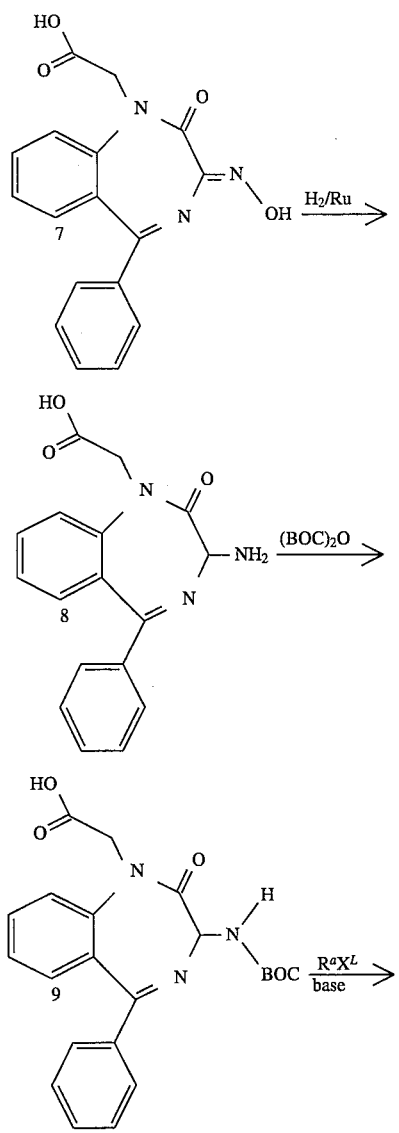

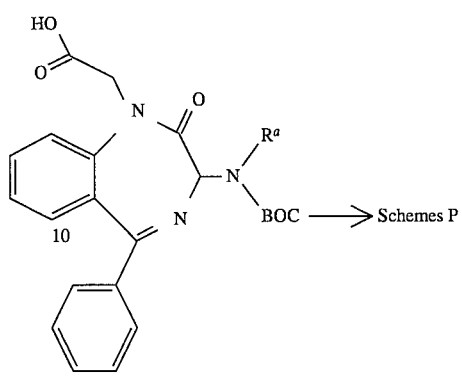

Compounds 9 and 10 can be further elaborated according to Schemes P. In general, the carboxylic acid function of 9 and 10 is reacted with a suitably protected amine component using standard solid phase (Scheme P) or solution phase peptide synthesis procedures. The BOC or other protecting group of N-3 of the benzodiazepinone is removed and the amine function then coupled with a third component, for example, a suitably protected amino acid, and then deprotected, again employing standard procedures. The resulting product is subsequently purified by chromatography or crystallization.

SCHEME P

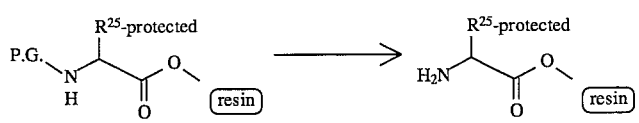

-continued
SCHEME P

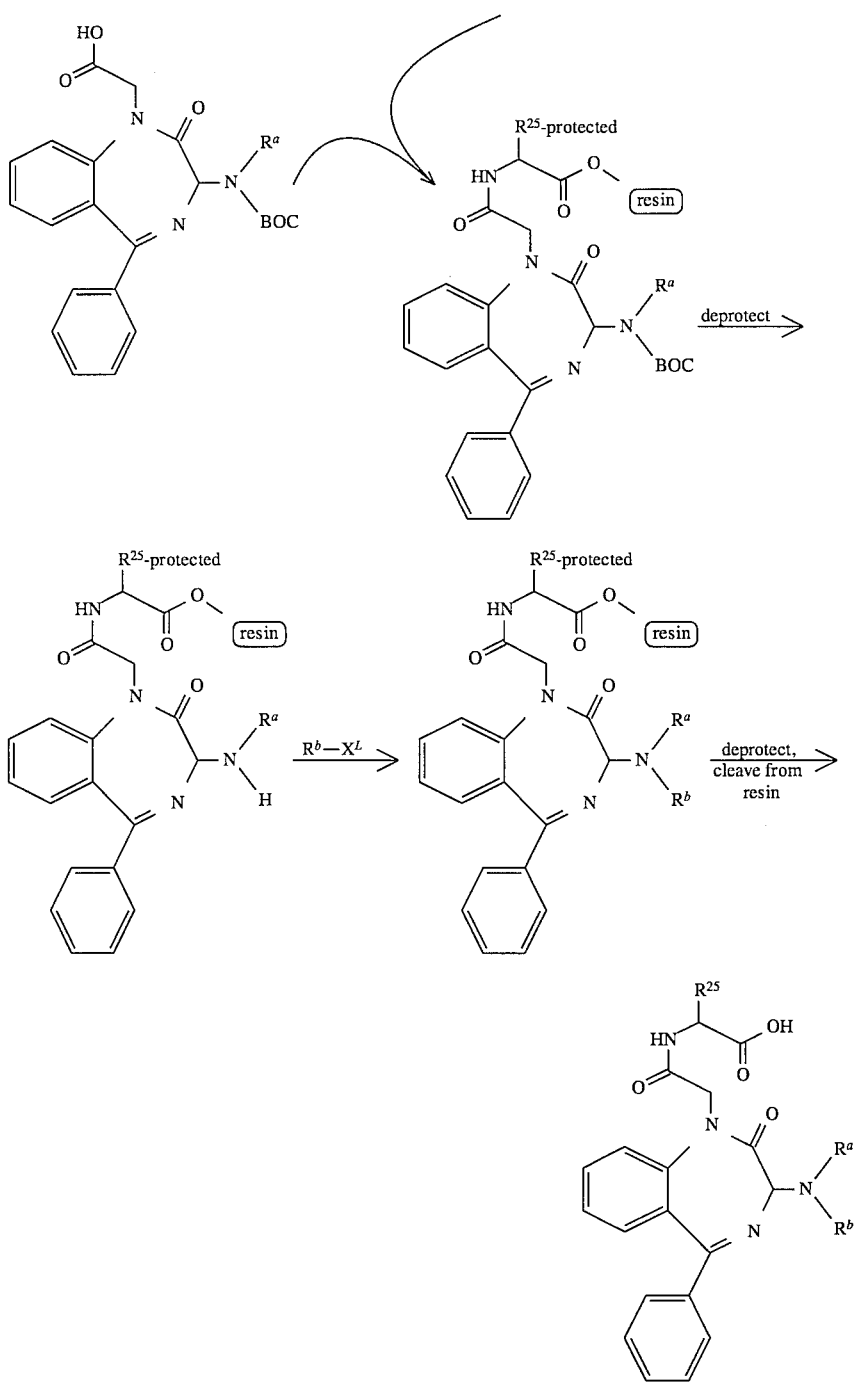

Alternatively, 3 may be directly alkylated with the "top" sidechain in one intact piece, as shown in Scheme Q. Reaction of 3 with an alkyl halide such as a suitably substituted benzyl bromide, alkyl bromide, in the presence of a base, preferably NaH or $Cs_2CO_3$, gives 11, which may be processed according to the reactions illustrated in Scheme I to provide the desired FPTase inhibitors.

SCHEME Q

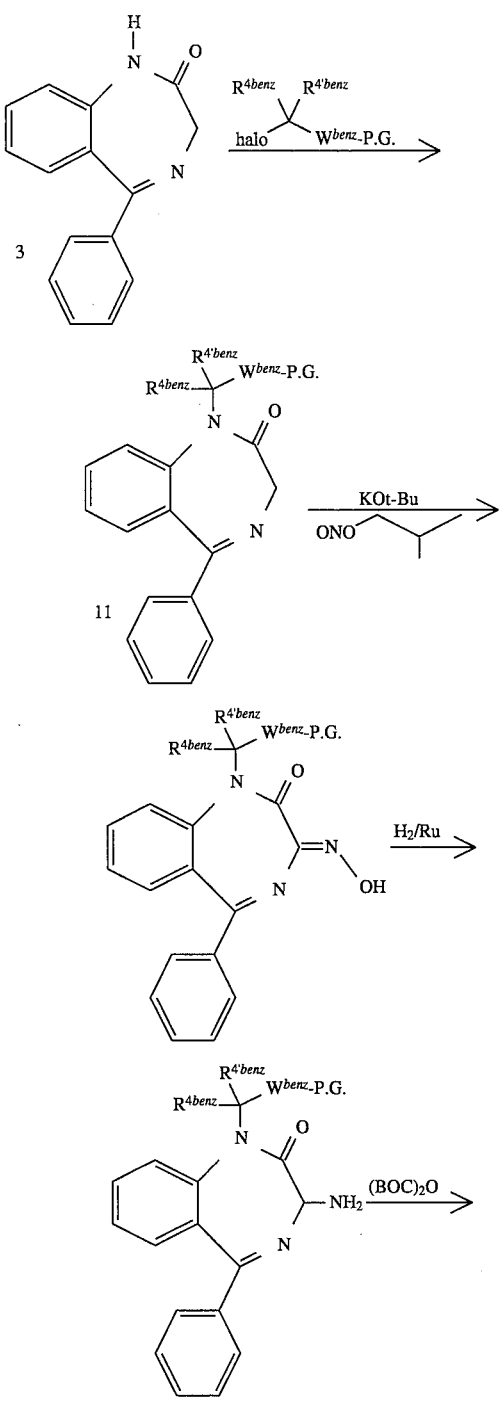

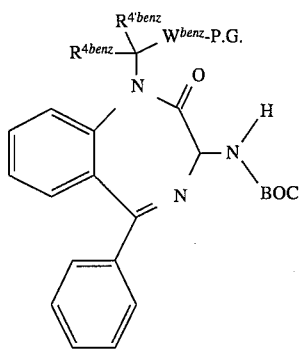

wherein P.G. is a suitably selected protecting group which is utilized if necessary.

The compounds of this invention inhibit Ras farnesyl transferase which catalyzes the first step in the post-translational processing of Ras and the biosynthesis of functional Ras protein. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 20 mg/kg of body weight per day, preferably of between 0.5 mg/kg of body weight to about 10 mg/kg of body weight per day.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof.

The standard workup referred to in the examples refers to solvent extraction and washing the organic solution with 10% citric acid, 10% sodium bicarbonate and brine as appropriate. Solutions were dried over sodium sulfate and evaporated in vacuo on a rotary evaporator.

Example 1

N-(1(S)-carboxy-3-methylthiopropyl)-3-(4-imidazolylmethyl)aminomethylbenzamide dihydrochloride Step A: Preparation of N-(1(S)-carbomethoxy-3-methylthiopropyl)-3-chloromethylbenzamide To a solution of (S) methionine methyl ester hydrochloride (10.56 g, 52.9 mmol) and 4-N-methylmorpholine (21.34 g, 211.6 mmol) under nitrogen in 200 mL of methylene chloride at 0° C. was added 3-chloro-methyl benzoyl chloride (10.00 g, 52.9 mmol) dropwise via syringe. After addition the cooling bath was removed and the resulting solution was stirred for 16 h at 20° C. The methylene chloride solution was extracted with 125 mL each of water, 2% potassium hydrogen sulfate, saturated sodium hydrogen carbonate, and saturated sodium chloride. The methylene chloride was dried over magnesium sulfate and concentrated in vacuo to the title compound as an oil. $^1$HNMR (300 MHz, $CDCl_3$)δ 7.85 (1H, s), 7.76 (1H, d, J=8 Hz), 7.56 (1H, d, J=8 Hz), 7.45 (1H, t, J=8 Hz), 6.96 (1H, d, J=7 Hz), 4.94 (1H, q, J=5 Hz), 4.62 (2H, s), 3.81 (3H, s), 2.60 (2H, t, J=8 Hz), 2.30 (1H, m), 2.15 (1H, m), 2.12 (3H, s).

Step B: Preparation of N-(1(S)-carbomethoxy-3-methylthiopropyl)-3-azidomethylbenzamide To a stirred solution of the product from Step A (13.52 g, 42.80 mmol) in 50 mL of dimethylsulfoxide under nitrogen was added lithium azide (2.3 g, 47.10 mmol). The solution was stirred for 2 h The reaction mixture was then partitioned with 300 mL of ethyl acetate and 200 mL of water. The ethyl acetate layer was washed with 125 mL of saturated sodium chloride, dried over magnesium sulfate and concentrated in vacuo to afford the title compound as an oil. $^1$HNMR (300 MHz, $CDCl_3$)δ 7.75 (2H, m), 7.47 (2H, m), 7.02 (1H, d, J=8 Hz), 4.94 (1H, q, J=5 Hz), 4.41 (2H, s), 3.80 (3H, s), 2.60 (2H, t, J=6 Hz), 2.30 (1H, m), 2.15 (1H,m), 2.11 (3H, s).

Step C: Preparation of N-(1(S)-carbomethoxy-3-methylthiopropyl)-3-aminomethylbenzamide To a solution of the product from Step B (11.8 g, 35.08 mmol) in 150 mL of methanol under nitrogen was added 1.5 g 10% palladium on carbon. Hydrogen was applied to the mixture at 1 atmosphere for 1.5 h. The reaction mixture was filtered and concentrated in vacuo to obtain 10.3 g (34.76 mmol) of crude product as an oil. The crude product was chromatographed on 500 g of silica gel with chloroform/methanol 95/5 as eluant to afford the title compound as an oil. $^1$HNMR (300 MHz, $CDCl_3$)δ 7.78 (1H, s), 7.68 (1H, d, J=7 Hz), 7.47 (1H, d, J=7 Hz), 7.40 (1H, t, J=8 Hz), 7.02 (1H, d, J=7 Hz), 4.93 (1H, q, J=5 Hz), 3.92 (2H, s), 3.79 (3H, s), 2.59 (2H, t, J=8 Hz), 2.24 (1H, m), 2.12 (1H, m), 2.10 (3H, s), 1.85 (2H,s).

Step D: Preparation of N-(1(S)-carbomethoxy-3-methylthiopropyl) 3-[(1-triphenylmethyl)-4-imidazolylmethyl] aminomethyl benzamide To a solution of the product from Step C (0.228 g, 0.767 mmol) in 10 mL of 1,2-dichloroethane was added glacial acetic acid dropwise until a pH 5.5 was achieved. To this mixture at 20° C. was added 0.5 g of crushed 4 Å molecular sieves, sodium triacetoxyborohydride (0.487 g, 2.30 mmol), and 1-(triphenylmethyl)-4imidazole carboxaldehyde (0.130 g, 0.384 mmol). The resulting solution was stirred for 12–72 h. The reaction mixture was filtered through celite and partitioned with 125 mL of water and 150 mL of ethyl acetate. The ethyl acetate layer was washed with 125 mL each of saturated sodium hydrogen carbonate and saturated sodium chloride, dried over magnesium sulfate, and concentrated in vacuo to yield 0.363 g of crude product. The crude product was chromatographed on silica gel eluting with chloroform/methanol 95/5 to afford the title compound. $^1$HNMR (300 MHz, CDCl$_3$)δ 7.83 (1H, s), 7.71 (1H, d, J=7 Hz), 7.40 (4H, m), 7.32 (8H, m), 7.25 (1H, s), 7.12 (7H, m), 6.71 (1H, s), 4.93 (1H, q, J=5 Hz), 3.85 (2H, s), 3.77 (3H, s), 3.71 (2H, s), 2.58 (2H, t, J=8 Hz), 2.25 (1H, m), 2.10 (1H, m), 2.09 (3H, s).

Step E. Preparation of N-(1(S)-carbomethoxy-3-methylthiopropyl)-3-(4-imidazolylmethyl)aminomethylbenzamide dihydrochloride To a solution of the product from Step D (0.220 g, 0.356 mmol) in 10 mL of methylene chloride was added triethylsilane (0.165 g, 1.42 mmol) and 5 mL of trifluoroacetic acid. The solution was stirred for 45 min, evaporated in vacuo, and partitioned with hexane and 0.1% trifluoroacetic acid in water:methanol 2:1. The 0.1% trifluoroacetic acid/water-methanol solution was injected directly onto a Delta-Pak (C-18, 100 Å, 15 mm, 40 mm×100 mm) prep HPLC column. The gradient at 40 mL/min. was 100% 0.1% TFA/water for 5 min. followed by 95% 0.1% TFA/water :5% 0.1% TFA/acetonitrile to 70% 0.1% TFA/water:30.% 0.1% TFA/acetonitrile over a period of 40 min. The pure fractions were pooled, evaporated in vacuo to near dryness, and then taken up in 5 mL of water. This water solution was passed through a 1.2 gm. column of Bio-Rad AG 3-X4 chloride anion exchange resin. The resulting aqueous column eluant was lyophillized overnight to yield the title compound as a solid. $^1$HNMR (300 MHz, CD$_3$OD)δ 9.04 (1H, s), 8.06 (1H, s), 7.96 (1H, d, J=8 Hz), 7.83 (1H, s), 7.76 (1H, d, J=8 Hz), 7.63 (1H, t, J=8 Hz), 4.81 (1H, q, J=5 Hz), 4.52 (2H, s), 4.42 (2H, s), 3.77 (3H, s), 2.63 (2H, m), 2.22 (1H, m), 2.16 (1H, m), 2.13 (3H, s). FAB mass spectrum m/e 377 (m+1).

Analysis calculated for C$_{18}$H$_{24}$N$_4$O$_3$S•3.3 HCl: C, 43.57; H, 5.55; N, 11.29. Found: C, 43.56; H, 5.54; N, 11.82.

Step F: Preparation of N-(1(S)-carboxy-3-methylthiopropyl)-3-(4-imidazolylmethyl)aminomethyl benzamide dihydrochloride The product from Step E (0.030 g, 0.067 mmol) was dissolved in 5 mL of methanol and 3 mL of 5% sodium hydroxide and stirred for 1 h under nitrogen. The reaction mixture was injected directly onto a preparative reverse phase HPLC column with conditions identical as in the preparation of the compound in Step E. Pure fractions were pooled, evaporated in vacuo, and the sample was converted to the hydrochloride salt as before. Lyophillization overnight afforded 0.022 g (0.051 mmol) of the title compound as a solid. $^1$HNMR (300 MHz, CD$_3$OD)δ 9.06 (1H, s), 8.06 (1H, s), 7.96 (1H, d, J=8 Hz), 7.83 (1H, s), 7.76 (1H, d, J=8 Hz), 7.61 (1 H, t, J=8 Hz), 4.78 (1H, q, J=5 Hz), 4.53 (2H, s), 4.47 (2H, s), 2.63 (2H, m), 2.25 (1H, m), 2.15 (1H, m), 2.13 (3H, s). FAB mass spectrum m/e 363 (m+1).

Analysis calculated for C$_7$H$_{22}$N$_4$O$_3$S•3.3 HCl•0.5 H$_2$O: C,41.57; H, 5.40; N, 11.41. Found: C, 41.54; H, 5.42; N, 11.05.

Example 2

N-(1(S)-carboxy-3-methylthiopropyl)-3-[N,N-bis(4-imidazolemethyl)aminomethyl]benzamide dihydrochloride Step A: Preparation of N-(1(S)-carbomethoxy-3-methylthiopropyl)-3-[N,N-bis(1-triphenylmethyl)-4-imidazolylmethyl]-aminomethyl-benzamide To a solution of the product from Example 1, Step C (0.100 g, 0.357 mmol) in 10 mL of 1,2-dichloroethane was added glacial acetic acid dropwise until the pH was 5.5. To this mixture at 20° C. was added 0.5 g of crushed 4 Å sieves, sodium triacetoxyborohydride (0.226 g, 2.30 mmol), and 1-(triphenylmethyl)-4-imidazole carboxaldehyde (0.130 g, 1.07 mmol). The resulting solution was stirred for 12–72 h. The reaction mixture was filtered through celite and partitioned with 125 mL of water and 150 mL of ethyl acetate. The ethyl acetate layer was washed with 125 mL each of saturated sodium hydrogen carbonate and saturated sodium chloride, dried over magnesium sulfate, and concentrated in vacuo to yield the title compound.

Step B: Preparation of N-(1(S)-carbomethoxy-3-methylthiopropyl)-3-[N,N-bis(4-imidazolylmethyl)aminomethyl] benzamide dihydrochloride To a solution of the product from Step A (0.320 g, 0.341 mmol) in 10 mL of methylene chloride was added triethylsilane (0.159 g, 1.36 mmol) and 5 mL of trifluoroacetic acid. The solution was stirred for 45 min, evaporated, and partitioned between hexane and 0.1% TFA in water-methanol 2:1. The 0.1% TFA/water:methanol solution was injected directly onto a Delta-Pak (C-18, 100 Å, 15 mm, 40 mm×100 mm) preparative HPLC column. The gradient at 40 mL/min was 100% 0.1% TFA/water for 5 min followed by 95% 0.1% TFA/water to 60% 0.1% TFA/water :40% 0.1% TFA/acetonitrile over 40 min. The pure fractions were pooled, evaporated to near dryness, and then taken up in 5 mL of water. The aqueous solution was passed through a 1.2 gm. column of Bio-Rad AG 3-X4 chloride anion exchange resin. The resulting aqueous column eluant was lyophillized overnight to yield the title compound as a solid. $^1$HNMR (300 MHz, CD$_3$OD)δ 8.92 (2H, s), 7.94 (1H, s), 7.78 (1H, d, J=8 Hz), 7.62 (2H, s), 7.58 (1H, d, J=8 Hz), 7.44 (1H, t, J=8 Hz), 4.81 (1H, q, J=5 Hz), 4.06 (4H, s), 3.93 (2H, s), 3.77 (3H, s), 2.63 (2H, m), 2.22 (1H, m), 2.16 (1H, m), 2.13 (3H, s ). FAB mass spectrum m/e 457 (m+1).

Analysis calculated for C$_{22}$H$_{28}$N$_6$O$_3$S•4.8 HCl•0.2 H$_2$O: C, 41.66; H, 5.28; N, 13.25. Found: C, 41.62; H, 5.27; N, 13.02

Step C: Preparation of N-(1(S)-carboxy-3-methylthiopropyl)-3-[N,N-bis(4-imidazolemethyl)aminomethyl]benzamide dihydrochloride The compound from Step B (0.035 g, 0.052 mmol) was dissolved in 5 mL of methanol and 3 mL of 5% sodium hydroxide and stirred for 1 hr under nitrogen. The reaction mixture was injected directly onto a preparative HPLC column with conditions identical as in Step B. Pure fractions were pooled, evaporated, and the sample converted to the hydrochloride salt as before. Lyophilization overnight afforded the title compound as a solid. $^1$HNMR (300 MHz, CD$_3$OD) δ 8.88 (2H, s), 7.87 (1H, s), 7.75 (1H, d, J=8 Hz), 7.55 (1H, s), 7.50 (1H, d, J=8 Hz), 7.42 (1H, t, J=8 Hz), 4.78 (1H, q, J=5 Hz), 3.88 (4H, s), 3.77 (2H, s), 2.63 (2H, m), 2.25 (1H, m), 2.15 (1H, m), 2.13 (3H, s). FAB mass spectrum m/e 443 (m+1).

Analysis calculated for C$_{21}$H$_{26}$N$_6$O$_3$S•5.4 HCl•1.5 H$_2$O: C, 37.91; H, 5.21; N, 12.63. Found: C, 37.97; H, 5.22; N, 12.37.

Example 3

N-(1(S)-carboxy-3-methylthiopropyl) 3-[(4-imidazolylmethyl)-N-methylaminomethyl]benzamide dihydrochloride Step A: Preparation of Methyl 3-chloromethyl benzoate To a solution of triethylamine (11.0 mL) in methanol (150 mL) at 0° C. was added 3-chloromethylbenzoyl chloride (5.0 g) dropwise. After stirring at 20° C. for 0.5 h the solution was concentrated in vacuo. The residue was partitioned with 125 mL of water and 150 mL of ethyl acetate. The ethyl acetate layer was washed with 125 mL each of saturated sodium hydrogen carbonate, 2% potassium hydrogen sulfate and saturated sodium chloride, dried over magnesium sulfate, and concentrated in vacuo to yield the title compound. $^1$HNMR (300 MHz, CDCl$_3$) δ 8.07 (1H, s), 7.99 (1H, d, J=8 Hz), 7.59 (1H, d, J=8 Hz), 7.43 (1H, t, J=8 Hz), 4.62 (2H, s), 3.92 (3H, s).

Step B: Preparation of Methyl 3-azidomethylbenzoate

Starting with the product from Step A the method used in Step B of Example 1 was used to prepare the title compound.

Step C: Preparation of Methyl 3-aminomethyl benzoate

Starting with the product from Step B the method used in Step C of Example 1 was used to prepare the title compound.

Step D: Preparation of Methyl 3-(t-butyloxycarbonyl)aminomethyl benzoate

To a solution of the product from Step C (1.14 g) in methylene chloride (50 mL) was added triethylamine (2.90 mL) and di-tert-butyl dicarbonate (1.67 g) and the mixture was stirred 16 h. The solution was partitioned with water and methylene chloride. The methylene chloride layer was washed with saturated sodium hydrogen carbonate, 2% potassium hydrogen sulfate and saturated sodium chloride, dried over magnesium sulfate, and concentrated in vacuo to yield 1.71 g of the crude product. Chromotography on silica gel with hexane/ethyl acetate 9/1 yielded the title compound. $^1$HNMR (300 MHz, CDCl$_3$) δ 7.95 (1H, s), 7.93 (1H, d, J=8 Hz), 7.49 (1H, d, J=8 Hz), 7.41 (1H, t, J=8 Hz), 4.90 (1H, b), 4.37 (2H, d, J=6 Hz), 3.92 (3H, s), 1.45 (9H, s).

Step E: Preparation of Methyl 3-[(t-butyloxycarbonyl)-N-methylaminomethyl]benzoate To a solution of the product from Step E (1.42 g) in dimethylformamide (30 mL) at 0° C. was added sodium hydride (0.43 g, 60% dispersion in minerol oil). After stirring for 0.5 h methyl iodide (0.40 mL) was added and the mixture was stirred 16 h at 20° C. The solution was concentrated in vacuo and the residue was partitioned between ethyl acetate and water. The ethyl acetate layer was washed with saturated sodium hydrogen carbonate, 2% potassium hydrogen sulfate and saturated sodium chloride, dried over magnesium sulfate, and concentrated in vacuo to yield the crude product. Chromatography on silica gel with hexane/ethyl acetate 9/1 yielded 0.35 g of the title compound. $^1$HNMR (300 MHz, CDCl$_3$) δ 7.93 (2H, m), 7.42 (2H, m), 4.45 (2H, s), 3.92 (3H, s), 2.83 (3H, d), 1.47 (9H, s).

Step F: Preparation of 3-[(t-butyloxycarbonyl)-N-methylaminomethyl]benzoic acid

To a solution of the product from Step E (0.35 g) in methanol was added 5% sodium hydroxide. After stirring for 2 h the methanol was evaporated and the aqueous layer was adjusted to pH 3 with 2% potassium hydrogen sulfate. The aqueous layer was extracted with ethyl acetate several times. The ethyl acetate layer was washed with saturated sodium chloride, dried over magnesium sulfate, and concentrated in vacuo to yield the title compound.

Step G: Preparation of N-(1 (S)-carbomethoxy-3-methylthiopropyl)-3-[(t-butyloxycarbonyl)-N-methylaminomethyl]benzamide To a solution of the product from Step F (0.27 g) in dimethylformamide (10 mL) was added hydroxybenzotriazole (0.16 g), EDC (0.19 g), N-methylmorpholine (0.40 mL), and (S) methione methyl ester hydrochloride (0.203 mg). After stirring for 2 h the solution was concentrated in vacuo and the residue was partitioned with water and ethyl acetate. The ethyl acetate layer was washed with saturated sodium hydrogen carbonate, 2% potassium hydrogen sulfate and saturated sodium chloride, dried over magnesium sulfate, and concentrated in vacuo to yield the title compound. $^1$HNMR (300 MHz, CDCl$_3$) δ 7.70 (2H, s), 7.40 (2H, m), 6.95 (1H, d, J=7 Hz), 4.94 (1H, q, J=7 Hz), 4.45 (2H, s), 3.81 (3H, s), 2.82 (3H, d), 2.59 (2H, m), 2.30 (1H, m), 2.13 (1H, m), 2.12 (3H, s), 1.46 (9H, s).

Step H: Preparation of N-(1(S)-carbomethoxy-3-methylthiopropyl)-3-(N-methylaminomethyl)benzamide trifluoroacetate To a solution of the product from Step G in methylene chloride was added trifluoroacetic acid (33% by volume). After stirring for 1 h the solution was concentrated in vacuo to yield the title compound.

Step I: Preparation of N-(1(S)-carbomethoxy-3-methylthiopropyl)-3-[(1-triphenylmethyl)-4-imidazolylmethyl-N-methylaminomethyl]benzamide Starting with the product from Step H (0.18 g) the method described in Step D of Example 1 was used to prepare the title compound.

Step J: Preparation of N-(1(S)-carbomethoxy-3-methylthiopropyl)-3-[(4-imidazolylmethyl)-N-methyl-minomethyl]benzamide dihydrochloride Starting with the compound from Step I (0.24 g) the method described in Step E of Example 1 was used to prepare the title compound. FAB mas spectrum m/e 391 (m+1).

Analysis for C$_{19}$H$_{26}$N$_4$O$_3$S•5.0 HCl•0.5 H$_2$O: Calculated: C, 39.32; H, 5.56; N, 9.65; Found: C, 39.33; H, 5.57; N, 9.38.

Step K: Preparation of N-(1(S)-carboxy-3-methylthiopropyl)-3-[(4-imidazolemethyl)-N-methyl-aminomethyl]benzamide dihydrochloride Starting with the compound from Step J (0.035 g) the method described in Step F of Example 1 was used to prepare the above title compound. FAB mas spectrum m/e 377 (m+1).

Analysis for C$_{18}$H$_{24}$N$_4$O$_3$S•3.70 HCl•0.2 H$_2$O: Calculated C, 42.05; H, 5.51; N, 10.90; Found: C, 42.09; H, 5.49; N, 10.70.

Example 4

N-(1(S)-carboxy-3-methylthiopropyl) 4-[(4-imidazolylmethyl)amino]benzamide dihydrochloride Step A: Preparation of 4-t-butyloxycarbonyl- aminobenzoic acid Starting with 4-aminobenzoic acid (2.00 g) dissolved in tetrahydrofuran (50 mL) and 5% sodium hydroxide (15 mL) the method described in Step D of Example 3 was used to prepare the title compound. After extractive work up obtained the title compound. $^1$HNMR (300 MHz, CDCl$_3$) δ 8.04 (2H, d, J=9 Hz), 7.46 (2H, d, J=9 Hz), 6.75 (1H, s), 1.46 (9H, s).

Step B: Preparation of N-(1(S)-carbomethoxy-3-methylthiopropyl)-4-(t-butyloxycarbonyl)aminobenzamide To a solution of the product from Step A (0.5 g) in dimethylformamide (20 mL) was added hydroxybenzotriazole (0.37 g), EDC (0.51 g), N-methylmorpholine 0.8 mL), and (S) methione methyl ester hydrochloride (0.49 g). After stirring for 16 h the solution was concentrated in vacuo and the residue was partitioned with water and ethyl acetate. The ethyl acetate layer was washed with saturated sodium hydrogen carbonate, 2% potassium hydrogen sulfate and saturated sodium chloride, dried over magnesium sulfate, and concentrated in vacuo to yield the title compound.

Step C: Preparation of N-(1(S)-carbomethoxy-3-methylthiopropyl)-4-aminobenzamide To a solution of the product from Step B in methylene chloride was added trifluoroacetic acid (33% by volume). After stirring for 1 h the solution was concentrated in vacuo to yield the trifluoroacetate salt of the product (0.59 g). This product was partioned between ethyl acetate and saturated sodium bicarbonate. The ethyl acetate layer was washed with saturated sodium chloride, dried over magnesium sulfate, and concentrated in vacuo to yield the title compound. $^1$HNMR (300 MHz, CDCl$_3$) δ 7.64 (2H, d, J=8 Hz), 6.75 (1H, d, J=8 Hz), 6.65 (2H, d, J=8 Hz), 4.90 (1H, q, J=5 Hz), 3.78 (3H, s), 2.57 (2H, m), 2.27 (1H, m), 2.08 (4H, m).

Step D: Preparation of N-(1(S)-carbomethoxy-3-methylthiopropyl)-4-[(1-triphenylmethyl)-4-imidazolylmethyl]aminobenzamide Starting with the product from Step C (0.07 g) the method described in Step D of Example 1 was used to prepare the title compound.

Step E: Preparation of N-(1(S)-carbomethoxy-3-methylthiopropyl)-4-(4-imidazolylmethyl)aminobenzamide dihydrochloride Starting with the product from Step D (0.24 g) the method described in Step E of Example 1 was used to prepare the title compound. FAB mas spectrum m/e 363 (m+1).

Analysis for C$_{17}$H$_{22}$N$_4$O$_3$S•2.8 HCl: Calculated: C, 43.99; H, 5.39; N, 12.07; Found: C, 43.94; H, 5.37; N, 12.24.

Step F: Preparation of N-(1(S)-carboxy-3-methylthiopropyl)-4-[(4-imidazolylmethyl)amino]benzamide dihydrochloride Starting with (5) (0.035 g) the method described in Step F of Example 1 was used to prepare the title compound. FAB mas spectrum m/e 349 (m+1).

Analysis for C$_{16}$H$_{20}$N$_4$O$_3$S•3.10 HCl•1.2 H$_2$O: Calculated: C, 39.91; H, 5.13; N, 11.63; Found: C, 39.87; H, 5.12; N, 11.22.

Using the appropriate staffing materials the methods described above for Example 4 were used to prepare Examples 5–7.

Example 5

N-(1(S)-carboxy-3-methylthiopropyl)-3-[(4-imidazolylmethyl)amino]benzamide dihydrochloride FAB mass spectrum m/e 349 (m+1).

Analysis for C$_{16}$H$_{20}$N$_4$O$_3$S•3.2 HCl: Calculated: C, 41.37; H, 5.03; N, 12.06; Found: C, 41.32; H, 4.92; N, 11.69.

Example 6

N-(1(S)-carbomethoxy-3-methylthiopropyl)-3-[(4-imidazolylpropyl)amino]benzamide dihydrochloride FAB mass spectrum m/e 391 (m+1).

Analysis for C$_{19}$H$_{26}$N$_4$O$_3$S•2.4 HCl•1.3 H$_2$O: Calculated: C, 45.53; H, 6.23; N, 11.18; Found: C, 45.51; H, 6.25; N, 11.10.

Example 7

N-(1(S)-Carboxy-3-methylthiopropyl)-3-[(4-imidazolylpropyl)amino]benzamide dihydrochloride FAB mass spectrum m/e 377 (m+1).

Analysis for C$_{18}$H$_{24}$N$_4$O$_3$S•3.0 HCl•0.5 H$_2$O: Calculated: C, 43.73; H, 5.71; N, 11.33; Found: C, 43.67; H, 5.71; N, 10.72.

Example 8

N-(1(S)-Carboxy-3-methylthiopropyl)-3-[N-(4-imidazolylmethyl)-N-(4nitrobenzyl)aminomethyl]benzamide ditrifluoroacetate Step A: N-(1(S)-Carbomethoxy-3-methylthiopropyl)-3-[N-(4-imidazolylymethyl)-N-(4-nitrobenzyl)aminomethyl]benzamide ditrifluoroacetate N-(1(S)-carbomethoxy-3-methylthiopropyl)-3-aminomethylbenzamide (0.104 g, 0.352 mmol) was dissolved in dichloroethane (5 mL). Crushed molecular sieves (0.209 g) and sodium triacetoxyborohydride (0.186 g, 0.881 mmol). The pH was about 7.5. 4-Nitrobenzaldehyde (0.0533 g, 0.352 mmol) was added plus 0.5 drop of acetic acid to bring the pH to about 7. The reaction was stirred 2 h under nitrogen at 20° C. 1-Triphenylmethylimidazolyly-4-carboxaldehyde (0.119 g, 0.352 mmol) was added to the reaction mixture with additional sodium triacetoxyborohydride and dichloroethane (2 mL). Triethylamine (5 drops) brought the pH to about 7. The reaction continued to stir at 20° C. under nitrogen overnight. The reaction was quenched with saturated sodium bicarbonate solution and let stir 20 min. It was then removed to a separatory funnel with copious amounts of ethyl acetate. The aqueous layer was removed and the organic phase was washed with saturated brine and dried over magnesium sulfate. The crude product was chromatographed on silica gel with 50% ethyl acetate in hexane. This chromatographed product was dissolved in dichloromethane (7 mL); triethylsilane (0.5 mL, 3.13 mmol) was added and then trifluoroacetic acid (3.5 mL). After 0.5 h at 20° C., the solvent was evaporated and the residue partitioned between hexane and water. The aqueous solution was purified by preparative reverse phase HPLC using a 100 mm Waters PrepPak® reverse phase column (DeltaPak™ C18, 50 µM, 100 Å) and pure product isolated by gradient elution using 80% 0.1% trifluoroacetic acid in water (Solvent A) and 20% 0.1% trifluoroacetic acid in acetonitrile (Solvent B) to 55% Solvent A and 45% Solvent B. The pure fractions were combined and the solvent evaporated, and the pure product was dissolved in water and lyophilized to give the title compound as a clear, pale yellow solid. $^1$HNMR (CD$_3$OD, 400 MHz) δ 8.78 (1H, br s), 8.18 (2H, d, J=8.6 Hz), 7.86 (1H br s), 7.74 (1H, br d, J=8 Hz), 7.64 (2H, d, J=8.6 Hz), 7.56 (1H, br d, J=8 Hz), 7.46 (1H, br s), 7.44 (1H, dd J=8, 8 Hz), 4.8 (1H, m), 3.74 to 3.79 (9H, m), 2.58 to 2.66 (2H, m), 2.23 (1H, m), 2.12 (1H, m), 2.10 (3H, s). FAB ms (m+1) 512.

Anal. Calc. for C$_{25}$H$_{29}$N$_5$O$_5$S•0.70 H$_2$O·3.30 TFA. Found: C, 42.12; H, 3.75, N, 7.91.

Step B: Preparation of N-(1(S)-carboxy-3-methylthiopropyl)-3-[N-(4-imidazolylymethyl)-N-(4-nitrobenzyl)aminomethyl]benzamide ditrifluoroacetate The product from Step A (0.045 g, 0.0608 mmol) was dissolved in methanol (4 mL) and 0.5 mL of 10% NaOH solution was added to take pH to about 12. Water (4 mL) was added. At 3 h reaction was purified and lyophilized according to the procedure described in Step A to the title compound as a white solid. $^1$HNMR (CD$_3$OD, 400 MHz) δ 8.78 (1H, br s), 8.18 (2H, d, J=8.6 Hz), 7.88 (1H, br s), 7.75 (1H, br d, J=8 Hz), 7.65 (2H, d, J=8.6 Hz), 7.55 (1H, br d, J=8 Hz), 7.46 (1H, br s), 7.43 (1H, dd, J=8, 8 Hz), 4.8 (1H, m), 3.80 (4H, br s), 3.75 (2H, br s), 2.58 to 2.68 (2H, m), 2.27 (1H, m), 2.13 (1H, m), 2.11 (3H, s). FAB ms (m+1) 498, Anal Calc. for C$_{24}$H$_{27}$N$_5$O$_5$S. 1.40 H$_2$O+3.20 TFA. Found: C, 41.16; H, 3.72; N, 8.11.

Example 9

N-(1(S)-carboxy-3-methylthiopropyl)-3-[N,N-bis-(4-nitrophenylmethyl)aminomethyl]benzamide dihydrochloride Step A: Preparation of N-(1(S)-carboxymethyl-3-methylthiopropyl)-3-[N,N-bis-(4-nitrophenylmethyl)]ditrifluoroacetate The product from Example 1, Step 3 (0.100 g, 0.337 mmol) was dissolved in dichloroethane (5 mL). p-Nitrobenzaldehyde, sodium triacetoxyborohydride (0.214 g, 1.01 mmol) and crushed molecular sieves were added, and the pH adjusted to 5.5 with acetic acid and triethylamine. The reaction was stirred at 20° C. overnight, quenched with saturated sodium bicarbonate, and partitioned between ethyl acetate and saturated sodium bicarbonate. The organic phase was washed with 2% potassium hydrogen sulfate, saturated sodium bicarbonate, saturated brine, and dried over magnesium sulfate. The crude product was purified by silica gel chromatography using 40% ethyl acetate in hexane. This product was further purified by preparative reverse phase HPLC using a gradient elution from 85 % water, 15% acetonitrile to 20% water over a period of 40 min. (solvents contained 0.1% trifluoroacetic acid). $^1$HNMR (300 MHz, CDCl$_3$) d 8.25(4H, d, J=8.5 Hz), 7.92 (1H, s), 7.80 (1H, d, J=7.6 Hz), 7.63 (4H, d, J=8.5 Hz).7.53 (m, 2H), 7.35 (1H, d, J=7.3 Hz), 4.94 (1H, bq, J=6.2 Hz), 3.98 (4H, s), 3.95 (2H, s), 3.82 (3H, s), 2.61 (2H, t, J=7.3 Hz), 2.30 (1H, m), 2.19 (1H, dt, J=15, 7.5 Hz), 2.11 (3H, s).

Analysis calculated for $C_{28}H_{30}N_4O_7S$•2.1 $CF_3CO_2H$•0.5 $H_2O$: C,47.45; H, 4.09; N, 6.87. Found: C, 47.44; H, 4.01;N, 6.91.

Step B: Preparation of N-(1(S)-carboxy-3-methylthiopropyl)-3-[N,N-bis-(4-nitrophenylmethyl)aminomethyl]benzamide ditrifluoroacetate The product from Step 1 (0.025 g) was hydrolyzed to the acid according to the procedure described in Example 1, Step 6. The title compound was obtained after purification by preparative reverse phase HPLC. FAB ms m/e (m+1) 553).

Analysis calculated for $C_{27}H_{28}N_4O_7S$•1.6 $CF_3CO_2H$•0.2 $H_2O$: C, 49.11; H, 4.09; N, 7.59. Found: C, 49.10; H, 3.93; N, 7.55.

Example 10

In vitro inhibition of ras farnesyl transferase

Assays of farnesyl-protein transferase. Partially purified bovine FPTase and Ras peptides (Ras-CVLS, Ras-CVIM and RAS-CAIL) were prepared as described by Schaber et al., *J. Biol. Chem.* 265:14701–14704 (1990), Pompliano, et al., *Biochemistry* 31:3800 (1992) and Gibbs et al., *PNAS U.S.A.* 86:6630–6634 (1989), respectively. Bovine FPTase was assayed in a volume of 100 µl containing 100 mM N-(2-hydroxy ethyl) piperazine-N'-(2-ethane sulfonic acid) (HEPES), pH 7.4, 5 mM MgCl$_2$, 5 mM dithiothreitol (DTT), 100 mM [$^3$H]-farnesyl diphosphate ([$^3$H]-FPP; 740 CBq/mmol, New England Nuclear), 650 nM Ras-CVLS and 10 µg/ml FPTase at 31 ° C. for 60 min. Reactions were initiated with FPTase and stopped with 1 ml of 1.0M HCL in ethanol. Precipitates were collected onto filter-mats using a TomTec Mach II cell harvestor, washed with 100% ethanol, dried and counted in an LKB β-plate counter. The assay was linear with respect to both substrates, FPTase levels and time; less than 10% of the [$^3$H]-FPP was utilized during the reaction period. Purified compounds were dissolved in 100% dimethyl sulfoxide (DMSO) and were diluted 20-fold into the assay. Percentage inhibition is measured by the amount of incorporation of radioactivity in the presence of the test compound when compared to the amount of incorporation in the absence of the test compound.

Human FPTase was prepared as described by Omer et al., *Biochemistry* 32:5167–5176 (1993). Human FPTase activity was assayed as described above with the exception that 0.1% (w/v) polyethylene glycol 20,000, 10 µM ZnCl$_2$ and 100 nM Ras-CVIM were added to the reaction mixture. Reactions were performed for 30 min., stopped with 100 µl of 30% (v/v) trichloroacetic acid (TCA) in ethanol and processed as described above for the bovine enzyme.

The compounds of the instant invention were tested for inhibitory activity against human FPTase by the assay described above and were found to have IC$_{50}$ of <100 µM.

Example 11

In vivo ras farnesylation assay

The cell line used in this assay is a v-ras line derived from either Rat1 or NIH3T3 cells, which expressed viral Ha-ras p21. The assay is performed essentially as described in DeClue, J. E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labelled in 3 ml methionine-free DMEM supplemeted with 10% regular DMEM, 2% fetal bovine serum and 400 mCi[$^{35}$S]methionine (1000 Ci/mmol). After an additional 20 hours, the cells are lysed in 1 ml lysis buffer (1% NP40/20 mM HEPES, pH 7.5/5 mM MgCl$_2$/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al., *J. Virol.* 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/ SDS/0.1M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

Example 12

In vivo growth inhibition assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of 1×10$^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

What is claimed is:

1. A compound which inhibits Ras farnesyl-transferase having the Formula I:

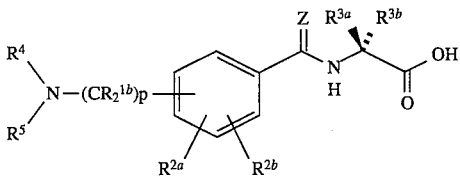

I wherein:

$R^{1a}$ and $R^{1b}$ are independently selected from:
a) hydrogen,
b) aryl, heterocycle, cycloalkyl, alkenyl, alkynyl, $R^{10}O—$, $R^{11}S(O)_m—$, $R^{10}C(O)NR^{10}—$, CN, $NO_2$, $(R^{10})_2N—C(NR^{10})—$, $R^{10}C(O)—$, $R^{10}OC(O)—$, $N_3$, $—N(R^{10})_2$, or $R^{11}OC(O)NR^{10}—$,
c) $C_1$–$C_6$ alkyl, and
d) $C_1$–$C_6$ alkyl substituted by a group selected from: aryl, heterocyclic, cycloalkyl, alkenyl, alkynyl, $R^{10}O—$, $R^{11}S(O)_m—$, $R^{10}C(O)NR^{10}—$, CN, $(R^{10})_2N—C(NR^{10})—$, $R^{10}C(O)—$, $R^{10}OC(O)—$, $N_3$, $—N(R^{10})_2$, or $R^{11}OC(O)—NR^{10}—$;

$R^{2a}$ and $R^{2b}$ are independently selected from:
a) hydrogen,
b) $C_1$–$C_6$ alkyl,
c) $C_1$–$C_6$ alkyl substituted by a group selected from: alkenyl, $R^{10}O—$, $R^{11}S(O)_m—$, $R^{10}C(O)NR^{10}—$, CN, $N_3$, $(R^{10})_2N—C(NR^{10})—$, $R^{10}C(O)—$, $R^{10}OC(O)—$, $—N(R^{10})_2$, or $R^{11}OC(O)NR^{10}—$,
d) aryl, heterocycle, cycloalkyl, alkenyl, $R^{10}O—$, $R^{11}S(O)_m—$, $R^{10}C(O)NR^{10}—$, CN, $NO_2$, $(R^{10})_2N—C(NR^{10})—$, $R^{10}C(O)—$, $R^{10}OC(O)—$, $N_3$, $—N(R^{10})_2$, or $R^{11}OC(O)NR^{10}—$, and
e) $C_1$–$C_6$ alkyl substituted with a a group selected from:
  i) aryl,
  ii) substituted aryl,
  iii) heterocyclic,
  iv) substituted heterocyclic,
  v) $C_3$–$C_{10}$ cycloalkyl, and
  vi) substituted $C_3$–$C_{10}$ cycloalkyl;

$R^{3a}$ and $R^{3b}$ are independently selected from:
a) a side chain of a naturally occurring amino acid,
b) an oxidized form of a side chain of a naturally occurring amino acid which is:
  i) methionine sulfoxide, or
  ii) methionine sulfone, and
c) a group selected from $C_1$–$C_{20}$ alkyl, $C_2$–$C_{20}$ alkenyl, $C_3$–$C_{10}$ cycloalkyl, aryl or heterocyclic group, the group which is substituted with a substituent is selected from F, Cl, Br, $N(R^{10})_2$, $NO_2$, $R^{10}O—$, $R^{11}S(O)_m—$, $R^{10}C(O)NR^{10}—$, CN, $(R^{10})_2N—C(NR^{10})—$, $R^{10}C(O)—$, $R^{10}OC(O)—$, $N_3$, $—N(R^{10})_2$, $R^{11}OC(O)NR^{10}—$ and $C_1$–$C_{20}$ alkyl,
d) a group selected from $C_1$–$C_{20}$ alkyl, $C_2$–$C_{20}$ alkenyl, $C_3$–$C_{10}$ cycloalkyl, aryl or heterocyclic group, and
e) $C_1$–$C_6$ alkyl substituted with a a group selected from:
  i) aryl,
  ii) substituted aryl,
  iii) heterocyclic,
  iv) substituted heterocyclic,
  v) $C_3$–$C_{10}$ cycloalkyl, and
  vi) substituted $C_3$–$C_{10}$ cycloalkyl;
or
$R^{3a}$ and $R^{3b}$ are combined to form $—(CH_2)_s—$ or $—(CH_2)_s—$ wherein one of the carbon atoms is replaced by a moiety selected from: O, $S(O)_m$, $—NC(O)—$, and $—N(COR^{10})—$;

$R^4$ and $R^5$ are independently selected from:
a) hydrogen, and
b)

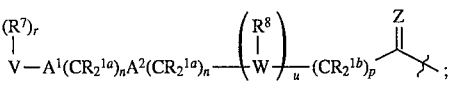

$R^7$ is independently selected from:
a) hydrogen,
b) aryl, heterocycle, cycloalkyl, alkenyl, alkynyl, perfluoroalkyl, F, Cl, Br, $R^{10}O—$, $R^{11}S(O)_m—$, $R^{10}C(O)NR^{10}—$, CN, $NO_2$, $R^{10}{}_2N—C(NR^{10})—$, $R^{10}C(O)—$, $R^{10}OC(O)—$, $N_3$, $—N(R^{10})_2$, or $R^{11}OC(O)NR^{10}—$,
c) $C_1$–$C_6$ alkyl, and
d) $C_1$–$C_6$ alkyl substituted by a group selected from: aryl, heterocycle, cycloalkyl, alkenyl, alkynyl, perfluoroalkyl, F, Cl, Br, $R^{10}O—$, $R^{11}S(O)_m—$, $R^{10}C(O)NH—$, CN, $H_2N—C(NH)—$, $R^{10}C(O)—$, $R^{10}OC(O)—$, $N_3$, $—N(R^{10})_2$, or $R^{10}OC(O)NH—$;

$R^8$ is selected from:
a) hydrogen,
b) alkenyl, alkynyl, perfluoroalkyl, F, Cl, Br, $R^{10}O—$, $R^{11}S(O)_m—$, $R^{10}C(O)NR^{10}—$, CN, $NO_2$, $(R^{10})_2N—C—(NR^{10})—$, $R^{10}C(O)—$, $R^{10}OC(O)—$, $N_3$, $—N(R^{10})_2$, or $R^{11}OC(O)NR^{10}—$,
c) $C_1$–$C_6$ alkyl, and
d) $C_1$–$C_6$ alkyl substituted by a group selected from: perfluoroalkyl, F, Cl, Br, $R^{10}O—$, $R^{11}S(O)_m—$, $R^{10}C(O)NR^{10}—$, CN, $(R^{10})_2N—C(NR^{10})—$, $R^{10}C(O)—$, $R^{10}OC(O)—$, $N_3$, $—N(R^{10})_2$, or $R^{11}OC(O)NR^{10}—$;

$R^{10}$ is independently selected from hydrogen, $C_1$–$C_6$ alkyl, benzyl and aryl;

$R^{11}$ is independently selected from $C_1$–$C_6$ alkyl and aryl;

$A^1$ and $A^2$ are independently selected from: a bond, $—CH=CH—$, $—C\equiv C—$, $—C(O)—$, $—C(O)NR^{10}—$, $—NR^{10}C(O)—$, O, $—N(R^{10})—$, $—S(O)_2N(R^{10})—$, $—N(R^{10})S(O)_2—$, or $S(O)_m$;

V is selected from:
a) hydrogen,
b) heterocyele,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$;

W is a heterocycle;

Z is independently $H_2$ or O;

m is 0, 1 or 2;

n is 0, 1, 2, 3 or 4;

p is 0, 1, 2, 3 or 4;

r is 0 to 5, provided that r is 0 when V is hydrogen;

s is 4 or 5; and u is 0 or 1;

or a pharmaceutically acceptable salt thereof.

2. A compound which inhibits Ras farnesyl-transferase having the Formula III:

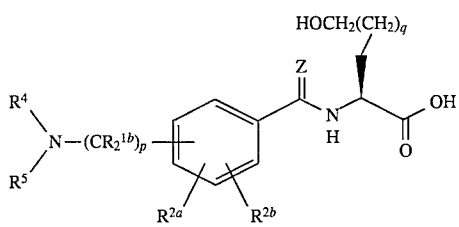

wherein:

$R^{1a}$ and $R^{1b}$ are independently selected from:
a) hydrogen,
b) aryl, heterocycle, cycloalkyl, alkenyl, alkynyl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, $N_3$, $N(R^{10})_2$, or $R^{11}OC(O)NR^{10}$—,
c) $C_1$–$C_6$ alkyl, and
d) $C_1$–$C_6$ alkyl substituted by a group selected from: aryl, heterocyclic, cycloalkyl, alkenyl, alkynyl, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, or $R^{11}OC(O)$—$NR^{10}$—;

$R^{2a}$ and $R^{2b}$ are independently selected from:
a) hydrogen.
b) $C_1$–$C_6$ alkyl;
c) $C_1$–$C_6$ alkyl substituted by a group selected from: alkenyl, $R^{10}O$—, $R^{11}S(O)_m$—, $R^{10}C(O)NR^{10}$—, CN, $N_3$, $(R^{10})_2N$—$C(NR^{10})$—, $R^{10}C(O)$—, $R^{10}OC(O)$—, —$N(R^{10})_2$, or $R^{11}OC(O)NR^{10}$—,
d) aryl, heterocycle, cycloalkyl, alkenyl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—, and
e) $C_1$–$C_6$ alkyl substituted with a a group selected from:
  i) aryl,
  ii) substituted aryl,
  iii) heterocyclic,
  iv) substituted heterocyclic,
  v) $C_3$–$C_{10}$ cycloalkyl, and
  vi) substituted $C_3$–$C_{10}$ cycloalkyl;

$R^4$ and $R^5$ are independently selected from:
a) hydrogen, and
b)

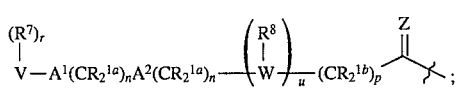

$R^7$ is independently selected from:
a) hydrogen,
b) aryl, heterocycle, cycloalkyl, alkenyl, alkynyl, perfluoroalkyl, F, Cl, Br, $R^{10}O$—, $R^{11}S(O)_m$—, $R^{10}C(O)NR^{10}$—, CN, $NO_2$, $R^{10}{}_2N$—$C(NR^{10})$—, $R^{10}C(O)$—, $R^{10}OC(O)$—, $N_3$, —$N(R^{10})_2$, or $R^{11}OC(O)NR^{10}$—,
c) $C_1$–$C_6$ alkyl, and
d) $C_1$–$C_6$ alkyl substituted by a group selected from: aryl, heterocycle, cycloalkyl, alkenyl, alkynyl, perfluoroalkyl, F, Cl, Br, $R^{10}O$—, $R^{11}S(O)_m$—, $R^{10}C(O)NH$—, CN, $H_2N$—$C(NH)$—, $R^{10}C(O)$—, $R^{10}OC(O)$—, $N_3$, —$N(R^{10})_2$, or $R^{10}OC(O)NH$—;

$R^8$ is selected from:
a) hydrogen,
b) alkenyl, alkynyl, perfluoroalkyl, F, Cl, Br, $R^{10}O$—, $R^{11}S(O)_m$—, $R^{10}C(O)NR^{10}$—, CN, $NO_2$, $(R^{10})_2N$—$C$—$(NR^{10})$—, $R^{10}C(O)$—, $R^{10}OC(O)$—, $N_3$, —$N(R^{10})_2$, or $R^{11}OC(O)NR^{10}$—,
c) $C_1$–$C_6$ alkyl, and
d) $C_1$–$C_6$ alkyl substituted by a group selected from: perfluoroalkyl, F, Cl, Br, $R^{10}O$—, $R^{11}S(O)m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—;

$R^{10}$ is independently selected from hydrogen, $C_1$–$C_6$ alkyl, benzyl and aryl;
$R^{11}$ is independently selected from $C_1$–$C_6$ alkyl and aryl;
$A^1$ and $A^2$ are independently selected from: a bond, —CH=CH—, —C≡C—, —C(O)—, —C(O)NR^{10}—, —NR^{10}C(O)—, O, —N(R^{10})—, —S(O)_2N(R^{10})—, —N(R^{10})S(O)_2—, or $S(O)_m$;

V is selected from:
a) hydrogen,
b) heterocycle,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$;
W is a heterocycle;
Z is independently $H_2$ or O;
m is 0, 1 or 2;
n is 0, 1, 2, 3 or 4;
p is 0, 1, 2, 3 or 4;
q is 0, 1 or 2;
r is 0 to 5, provided that r is 0 when V is hydrogen;
s is 4 or 5; and
u is 0 or 1;
or a pharmaceutically acceptable salt thereof.

3. The compound according to claim 1 of the formula Ia:

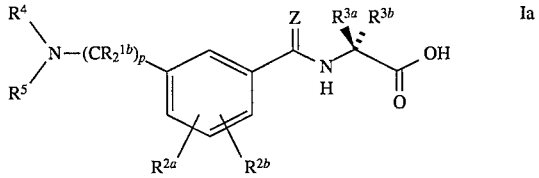

wherein:
$R^{1a}$ is independently selected from: hydrogen or $C_1$–$C_6$ alkyl;
$R^{1b}$ is independently selected from:
a) hydrogen,
b) aryl, heterocycle, cycloalkyl, $R^{10}O$—, —$N(R^{10})_2$ or alkenyl,
c) $C_1$–$C_6$ alkyl, and
d) $C_1$–$C_6$ alkyl substituted by a group selected from: aryl, heterocycle, cycloalkyl, alkenyl, $R^{10}O$—, or —$N(R^{10})_2$;

$R^{2a}$ is selected from:
a) hydrogen,
b) $C_1$–$C_6$ alkyl,
c) $C_1$–$C_6$ alkyl substituted by a group selected from: alkenyl, $R^{10}O$—, $R^{11}S(O)_m$—, $R^{10}C(O)NR^{10}$—, CN, $N_3$, $(R^{10})_2N$—$C(NR^{10})$—, $R^{10}C(O)$—, $R^{10}OC(O)$—, —$N(R^{10})_2$, or $R^{11}OC(O)NR^{10}$—, d) aryl, heterocycle, cycloalkyl, alkenyl, $R^{10}O—$, $R^{11}S(O)_m—$, $R^{10}C(O)NR^{10}—$, CN, $NO_2$, $(R^{10})_2N—C(NR^{10})—$, $R^{10}C(O)—$, $R^{10}OC(O)—$, $N_3$, $—N(R^{10})_2$, or $R^{11}OC(O)NR^{10}—$, and e) $C_1–C_6$ alkyl substituted with a a group selected from:
   i) aryl,
   ii) substituted aryl,
   iii) heterocyclic,
   iv) substituted heterocyclic,
   v) $C_3–C_{10}$ cycloalkyl, and
   vi) substituted $C_3–C_{10}$ cycloalkyl;

$R^{2b}$ is hydrogen;

$R^{3a}$ and $R^{3b}$ are independently selected from:
   a) a side chain of a naturally occurring amino acid,
   b) an oxidized form of a side chain of a naturally occurring amino acid which is:
      i) methionine sulfoxide, or
      ii) methionine sulfone,
   c) a group selected from $C_1–C_{20}$ alkyl, $C_2–C_{20}$ alkenyl, $C_3–C_{10}$ cycloalkyl, aryl or heterocyclic group, the group which is substituted with a substituent is selected from F, Cl, Br, $N(R^{10})_2$, $NO_2$, $R^{10}O—$, $R^{11}S(O)_m—$, $—R^{10}C(O)NR^{10}—$, CN, $(R^{10})_2N—C(NR^{10})—$, $R^{10}C(O)—$, $R^{10}OC(O)—$, $N_3$, $—N(R^{10})_2$, $R^{11}OC(O)NR^{10}—$ and $C_1–C_{20}$ alkyl,
   d) a group selected from $C_1–C_{20}$ alkyl, $C_2–C_{20}$ alkenyl, $C_3–C_{10}$ cycloalkyl, aryl or heterocyclic group, and
   e) $C_1–C_6$ alkyl substituted with a a group selected from:
      i) aryl,
      ii) substituted aryl,
      iii) heterocyclic,
      iv) substituted heterocyclic,
      v) $C_3–C_{10}$ cycloalkyl, and
      vi) substituted $C_3–C_{10}$ cycloalkyl;

$R^4$ and $R^5$ are independently selected from:
   a) hydrogen, and
   b)

$$V—A^1(CR_2^{1a})_n A^2(CR_2^{1a})_n \overset{(R^7)_r}{\underset{}{|}} \left(\overset{R^8}{\underset{}{|}} W\right)_u (CR_2^{1b})_p \overset{Z}{\diagup}\diagdown;$$

$R^7$ is independently selected from:
   a) hydrogen,
   b) $C_1–C_6$ alkyl, $C_2–C_6$ alkenyl, $C_2–C_6$ alkynyl, $C_1–C_6$ perfluoroalkyl, F, Cl, $R^{10}O—$, $R^{10}C(O)NR^{10}—$, CN, $NO_2$, $(R^{10})_2N—C(NR^{10})—$, $R^{10}C(O)—$, $R^{10}OC(O)—$, $—N(R^{10})_2$, or $R^{11}OC(O)NR^{10}—$, and
   c) $C_1–C_6$ alkyl substituted by $C_1–C_6$ perfluoroalkyl, $R^{10}O—$, $R^{10}C(O)NR^{10}—$, $(R^{10})_2N—C(NR^{10})—$, $R^{10}C(O)—$, $R^{10}OC(O)(—$, $—N(R^{10})_2$, or $R^{11}OC(O)NR^{10}13$ ;

$R^8$ is selected from:
   a) hydrogen,
   b) $C_2–C_6$ alkenyl, $C_2–C_6$ alkynyl, $C_1–C_6$ perfluoroalkyl, F, Cl, $R^{10}O—$, $R^{11}S(O)_m—$, $R^{10}C(O)NR^{10}—$, CN, $NO_2$, $(R^{10})_2N—C(NR^{10})—$, $R^{10}C(O)—$, $R^{10}OC(O)—$, $—N(R^{10})_2$, or $R^{11}OC(O)NR_{10}—$,
   c) $C_1–C_6$ alkyl; and
   d) $C_1–C_6$ alkyl substituted by a group selected from: $C_1–C_6$ perfluoroalkyl, F, Cl, $R^{10}O—$, $R^{11}S(O)_m—$, $R^{10}C(O)NR^{10}$, CN, $(R^{10})_2N—C(NR^{10})—$, $R^{10}C(O)—$, $R^{10}OC(O)—$, $—N(R^{10})_2$, or $R^{11}OC(O)NR^{10}—$;

$R^{10}$ is independently selected from hydrogen, $C_1–C_6$ alkyl, benzyl and aryl;

$R^{11}$ is independently selected from $C_1–C_6$ alkyl and aryl;

$A^1$ and $A^2$ are independently selected from: a bond, $—CH=CH—$, $—C\equiv C—$, $—C(O)—$, $—C(O)NR^{10}—$, O, $—N(R^{10})—$, or $S(O)_m$;

V is selected from:
   a) hydrogen,
   b) heterocycle selected from pyrrolidinyl, imidazolyl, pyridinyl, thiazolyl, pyridonyl, 2-oxopiperidinyl, indolyl, quinolinyl, isoquinolinyl, and thienyl,
   c) aryl,
   d) $C_1–C_{20}$ alkyl wherein from 0 to 4 carbon atoms are replaced with a a heteroatom selected from O, S, and N, and
   e) $C_2–C_{20}$ alkenyl, and provided that V is not hydrogen if $A^1$ is $S(O)_m$ and V is not hydrogen if $A^1$ is a bond, n is 0 and $A^2$ is $S(O)_m$;

W is a heterocycle selected from pyrrolidinyl, imidazolyl, pyridinyl, thiazolyl, pyridonyl, 2-oxopiperidinyl, indolyl, quinolinyl, or isoquinolinyl;

Z is independently $H_2$ or O;

m is 0, 1 or 2;

n is 0, 1, 2, 3 or 4;

p is 0, 1, 2, 3 or 4;

r is 0 to 5, provided that r is 0 when V is hydrogen; and u is 0 or 1;

or a pharmaceutically acceptable salt thereof.

4. The compound according to claim 2 of the formula IIIa:

$$\underset{R^5}{\overset{R^4}{\diagdown}}N—(CR_2^{1b})_p—\underset{R^{2a}\quad R^{2b}}{\text{[aryl ring]}}—\overset{Z}{\underset{H}{C}}—N\underset{H}{\overset{HOCH_2(CH_2)_q}{|}}\overset{}{C}H—\overset{O}{\underset{}{C}}—OH \quad \text{IIIa}$$

wherein:

$R^{1a}$ is independently selected from: hydrogen or $C_1–C_6$ alkyl;

$R^{1b}$ is independently selected from:
   a) hydrogen,
   b) aryl, heterocycle, cycloalkyl, $R^{10}O—$, $—N(R^{10})_2$ or alkenyl,
   c) $C_1–C_6$ alkyl, and
   d) $C_1–C_6$ alkyl substituted by a group selected from: aryl, heterocycle, cycloalkyl, alkenyl, $R^{10}O—$, or $—N(R^{10})_2$;

$R^{2a}$ is selected from:
   a) hydrogen,
   b) $C_1–C_6$ alkyl,
   c) $C_1–C_6$ alkyl substituted by a group selected from: alkenyl, $R^{10}O—$, $R^{11}S(O)m—$, $R^{10}C(O)NR^{10}—$, CN, $N_3$, $(R^{10})_2N—C(NR^{10})—$, $R^{10}C(O)—$, $R^{10}OC(O)—$, $—N(R^{10})_2$, or $R^{11}OC(O)NR^{10}—$,
   d) aryl, heterocycle, cycloalkyl, alkenyl, $R^{10}O—$, $R^{11}S(O)_m—$, $R^{10}C(O)NR^{10}—$, CN, $NO_2$, $(R^{10})_2N—C(NR^{10})—$, $R^{10}C(O)—$, $R^{10}OC(O)—$, $N_3$, $—N(R^{10})_2$, or $R^{11}OC(O)NR^{10}—$, and
   e) $C_1–C_6$ alkyl substituted with a a group selected from:
      i) aryl,
      ii) substituted aryl,
      iii) heterocyclic,
      iv) substituted heterocyclic,
      v) $C_3–C_{10}$ cycloalkyl, and vi) substituted $C_3-C_{10}$ cycloalkyl;
$R^{2b}$ is hydrogen;
$R^4$ and $R^5$ are independently selected from:
a) hydrogen, and
b)

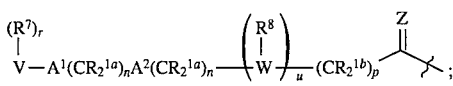

$R^7$ is independently selected from:
a) hydrogen,
b) $C_1-C_6$ alkyl, $C_2-C_6$ alkenyl, $C_2-C_6$ alkynyl, $C_1-C_6$ perfluoroalkyl, F, Cl, $R^{10}O-$, $R^{10}C(O)NR^{10}-$, CN, $NO_2$, $(R^{10})_2N-C(NR^{10})-$, $R^{10}C(O)-$, $R^{10}OC(O)-$, $-N(R^{10})_2$, or $R^{11}OC(O)NR^{10}-$, and
c) $C_1-C_6$ alkyl substituted by $C_1-C_6$ perfluoroalkyl, $R^{10}O-$, $R^{10}C(O)NR^{10}-$, $(R^{10})_2N-C(NR^{10})-$, $R^{10}C(O)-$, $R^{10}OC(O)-$, $-N(R^{10})_2$, or $R^{11}OC(O)NR^{10}-$;
$R^8$ is selected from:
a) hydrogen,
b) $C_2-C_6$ alkenyl, $C_2-C_6$ alkynyl, $C_1-C_6$ perfluoroalkyl, F, Cl, $R^{10}O-$, $R^{11}S(O)_m-$, $R^{10}C(O)NR^{10}-$, CN, $NO_2$, $(R^{10})_2N-C(NR^{10})-$, $R^{10}C(O)-$, $R^{10}OC(O)-$, $-N(R^{10})_2$, or $R^{11}OC(O)NR^{10}-$,
c) $C_1-C_6$ alkyl; and
d) $C_1-C_6$ alkyl substituted by a group selected from: $C_1-C_6$ perfluoroalkyl, F, Cl, $R^{10}O-$, $R^{11}S(O)_m-$, $R^{10}C(O)NR^{10}-$, CN, $(R^{10})_2N-C(NR^{10})-$, $R^{10}C(O)-$, $R^{10}OC(O)-$, $-N(R^{10})_2$, or $R^{11}OC(O)NR^{10}-$;
$R^{10}$ is independently selected from hydrogen, $C_1-C_6$ alkyl, benzyl and aryl;
$R^{11}$ is independently selected from $C_1-C_6$ alkyl and aryl;
$A^1$ and $A^2$ are independently selected from: a bond, $-CH=CH-$, $-C\equiv C-$, $-C(O)-$, $-C(O)NR^{10}-$, O, $-N(R^{10})-$, or $S(O)_m$;
V is selected from:
a) hydrogen,
b) heterocycle selected from pyrrolidinyl, imidazolyl, pyridinyl, thiazolyl, pyridonyl, 2-oxopiperidinyl, indolyl, quinolinyl, isoquinolinyl, and thienyl,
c) aryl,
d) $C_1-C_{20}$ alkyl wherein from 0 to 4 carbon atoms are replaced with a a heteroatom selected from O, S, and N, and
e) $C_2-C_{20}$ alkenyl, and
provided that V is not hydrogen if $A^1$ is $S(O)_m$ and V is not hydrogen if $A^1$ is a bond, n is 0 and $A^2$ is $S(O)_m$;
W is a heterocycle selected from pyrrolidinyl, imidazolyl, pyridinyl, thiazolyl, pyridonyl, 2-oxopiperidinyl, indolyl, quinolinyl, or isoquinolinyl;
Z is independently $H_2$ or O;
m is 0, 1 or 2;
n is 0, 1, 2, 3 or 4;
p is 0, 1, 2, 3 or 4;
q is 0, 1 or 2;
r is 0 to 5, provided that r is 0 when V is hydrogen; and
u is 0 or 1;
or a pharmaceutically acceptable salt thereof.

5. A compound which inhibits farnesyl-protein transferase which is:
N-(1(S)-carboxy-3-methylthiopropyl)-3-(4-imidazolylmethyl)aminomethylbenzamide
N-(1(S)-carboxy-3-methylthiopropyl)-3-[N,N-bis-(4-imidazolemethyl)aminomethyl]benzamide
N-(1(S)-carboxy-3-methylthiopropyl)3-[(4-imidazolylmethyl)-N-methylaminomethyl]benzamide
N-(1(S)-carboxy-3-methylthiopropyl)-4-[(4-imidazolylmethyl)amino]benzamide
N-(1(S)-carboxy-3-methylthiopropyl)-3-[(4-imidazolylmethyl) amino]benzamide
N-(1(S)-Carboxy-3-methylthiopropyl)-3-[(4-imidazolylpropyl) amino]benzamide
N-(1(S)-Carboxy-3-methylthiopropyl)-3-[N-(4-imidazolylmethyl)-N-(4-nitrobenzyl)aminomethyl]benzamide
N-(1(S)-carboxy-3-methylthiopropyl)-3-[N,N-bis-(4-nitrophenylmethyl)aminomethyl]benzamide or
or a pharmaceutically acceptable salt thereof.

6. A compound according to claim 5 which inhibits farnesyl-protein transferase which is:
N-(1(S)-carboxy-3-methylthiopropyl)-3-[N,N-bis-(4-nitrophenylmethyl)]aminomethylbenzamide

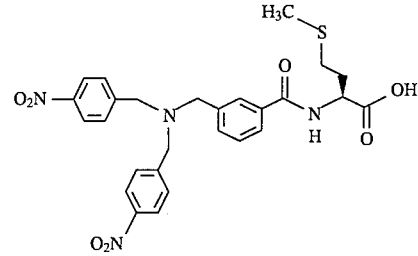

or a pharmaceutically acceptable salt thereof.

7. A compound according to claim 5 which inhibits farnesyl-protein transferase which is:
N-(1(S)-carboxy-3-methylthiopropyl)-3-[N,N-bis(4-imidazolemethyl)aminomethyl]benzamide

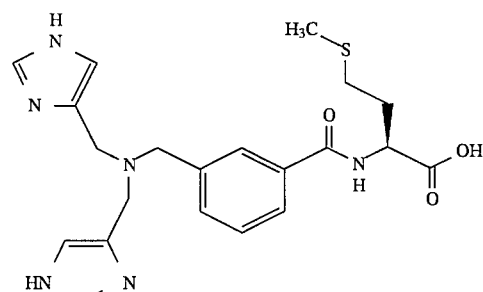

or a pharmaceutically acceptable salt thereof.

8. A compound according to claim 5 which inhibits farnesyl-protein transferase which is:

N-(1(S )-Carboxy-3-methylthiopropyl)-3-[N-(4-imidazoly-lymethyl)-N-(4-nitrobenzyl)aminomethyl]benzamide

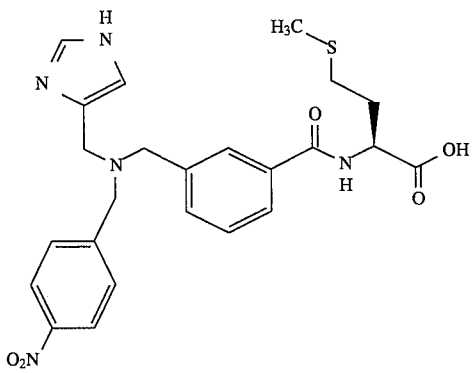

or a pharmaceutically acceptable salt thereof.

9. A pharmaceutical composition comprising a pharmaceutical carrier, and dispersed therein, a therapeutically effective amount of a compound of claim 1.

10. A pharmaceutical composition comprising a pharmaceutical carrier, and dispersed therein, a therapeutically effective amount of a compound of claim 2.

11. A pharmaceutical composition comprising a pharmaceutical carrier, and dispersed therein, a therapeutically effective amount of a compound of claim 5.

12. A method for inhibiting farnesylation of Ras protein which comprises administering to a mammal in need thereof a therapeutically effective amount of the composition of claim 9.

13. A method for inhibiting farnesylation of Ras protein which comprises administering to a mammal in need thereof a therapeutically effective amount of the composition of claim 10.

14. A method for inhibiting farnesylation of Ras protein which comprises administering to a mammal in need thereof a therapeutically effective amount of the composition of claim 11.

15. A method for treating cancer which comprises administering to a mammal in need thereof a therapeutically effective amount of a composition of claim 9.

16. A method for treating cancer which comprises administering to a mammal in need thereof a therapeutically effective amount of a composition of claim 10.

17. A method for treating cancer which comprises administering to a mammal in need thereof a therapeutically effective amount of a composition of claim 11.

* * * * *